(12) United States Patent
Leonardi et al.

(10) Patent No.: US 6,953,800 B2
(45) Date of Patent: *Oct. 11, 2005

(54) USE OF SELECTIVE ANTAGONISTS OF THE $\alpha_{1B}$-ADRENERGIC RECEPTOR FOR IMPROVEMENT OF SEXUAL DYSFUNCTION

(75) Inventors: Amedeo Leonardi, Milan (IT); Gianni Motta, Barlassina (IT); Rodolfo Testa, Vignate (IT); Giorgio Sironi, Pieve Emanuele (IT)

(73) Assignees: Recordati S.A. Chemical, Chiasso (CH); Pharmaceutical Company, Chiasso (CH)

( * ) Notice: Subject to any disclaimer, the term of this patent is extended or adjusted under 35 U.S.C. 154(b) by 116 days.

This patent is subject to a terminal disclaimer.

(21) Appl. No.: 09/935,288

(22) Filed: Aug. 22, 2001

(65) Prior Publication Data

US 2002/0161009 A1 Oct. 31, 2002

Related U.S. Application Data

(63) Continuation of application No. 09/565,842, filed on May 5, 2000, now Pat. No. 6,303,606.
(60) Provisional application No. 60/183,257, filed on Feb. 17, 2000.

(30) Foreign Application Priority Data

May 7, 1999 (IT) .......................................... MI99A0995

(51) Int. Cl.$^7$ ..................... A61K 31/519; C07D 419/00; C07D 403/00; C07D 241/36
(52) U.S. Cl. ....................... 514/249; 514/260; 544/284; 544/292; 544/355; 549/229
(58) Field of Search ................................ 514/249, 260; 544/284, 292, 355; 549/229

(56) References Cited

U.S. PATENT DOCUMENTS

| | | | |
|---|---|---|---|
| 5,403,842 A | 4/1995 | Leonardi et al. | ............ 514/252 |
| 5,474,994 A | 12/1995 | Leonardi et al. | ............ 514/218 |
| 5,605,897 A | 2/1997 | Beasley, Jr. et al. | ........ 514/220 |
| 5,700,364 A | 12/1997 | Rossen | ........................ 205/425 |

FOREIGN PATENT DOCUMENTS

| | | |
|---|---|---|
| EP | 0 611 248 A1 | 8/1994 |
| EP | 0 611 248 B1 | 8/1994 |
| WO | WO 95/25726 | 9/1995 |
| WO | WO 96/28142 | 9/1996 |
| WO | WO 97/11698 | 4/1997 |

OTHER PUBLICATIONS

Sanger, F., et al; "DNA Sequencing With Chain–Terminating Inhibitors";, *Proc. Natl. Acad. Sci*, vol. 74, No. 12; pp. 5463–5467 (Dec. 1977).

Schwinn, Debra A, et al; "Molecular Cloning and Expression of the cDNA for a Novel $\alpha_1$Adrenergic Receptor Subtype"; *J. of Biological Chemistry*; vol. 265, No. 14; pp. 8183–8189 (1990).

Sironi, Giorgio, et al., "Effects of Intracavernous Administration of Selective Antagonists of $\alpha-_1$Adrenoceptor Subtypes on Erection in Anesthetized Rats and Dogs", *J. Pharmacology and Experimental Therapeutics*, 292(3):974–981 (2000).

Taddei, Carlo, et al; "Affinity of Different $\alpha-_1$Agonists and Antagonists for the $\alpha_1$ Adrenoceptors of Rabbit and Rat Liver Membranes"; *Life Sciences*, vol. 53; pp. 177–181 (1993).

Testa, Rodolfo; "Characterization of $\alpha_1$–Adrenoceptor Subtypes In Prostate and Prostatic Urethra of Rat, Rabbit, Dog and Man"; *Eur. J. of Pharmacology*, vol. 249; pp. 307–315 (1993).

Testa, R., et al; "Pharmacological Characterization of the Uroselective Alpha–1 Antagonist Rec 15/2739 (SB 216469: Role of the Alpha–IL Adrenoceptor in Tissue Selectivity, Part II"; *J. of Pharmacology and Experimental Therapeutics*; vol. 281, No. 3; pp. 1284–1293 (1997).

Testa, R., et al; "REC 15/2739 (SB 216469):A Novel Prostate Selective $\alpha_1$–Adrenoceptor Antagonist"; *Pharmacology Communications*; vol. 6, Nos. 1–3; pp. 79–86 (1995).

Traish, Abdulmaged M., et al; "Identification of $\alpha_1$–Adrenergic Receptor Subtypes in Human Corpus Cavernosum Tissue and in Cultured Trabecular Smooth Muscle Cells"; *Humana Press Inc.*; vol. 5; pp. 145–157 (1995).

Traish, Abdulmaged M., et al; "A Heterogeneous Population of $\alpha_1$ Adrenergic Receptors Mediates Contraction of Human Corpus Cavernosum Smooth Muscle To Norepinephrine"; *J. of Urology*; vol. 153; pp. 222–227 (Jan. 1995).

Vaidyanathan, S., et al., "Prolonged Penile Erection Association with Terazosin in a Cervical Spinal Cord Injury Patient", *Letters to the Editor, Regional Spinal Injuries Centre, District General Hospital, Southport, Merseyside, PR8 6PN, UK*, 36(11)805 (1998).

Véonneau–Longueville, F., et al; Expression of $\alpha 1$ Adrenoceptor Subtypes in Rat Corpus Cavernosum; *Int. J. of Impotence Research*; vol. 10; pp. 187–194 (1998).

Vieira, Jeffrey, et al., "The pUC Plasmids, An M13mp7–Derived System For Insertion Mutagenesis and Sequencing With Synthetic Universal Primers", *Elsevier Biomedical Press, Gene*; vol. 19; pp. 259–268 (1982).

(Continued)

*Primary Examiner*—Mukund J. Shah
*Assistant Examiner*—Tamthon N. Truong
(74) *Attorney, Agent, or Firm*—Darby & Darby (57) ABSTRACT

Described is the use in the treatment of either male or female sexual dysfunction of selective antagonists of the $\alpha_{1B}$-adrenergic receptor and the pharmaceutical compositions containing them as compounds capable of helping the sexual act avoiding at the same time excessive side effects due to acute hypotension.

7 Claims, 2 Drawing Sheets-

OTHER PUBLICATIONS

Yang–Feng, T.L., et al; "The Terminal Deoxynucleotidyl-transferase Gene Is Located On Human Chromosome 10 (10q23→124) and On Mouse Chromosome 19"; *Cytogenet Cell Genet,* vol. 43; pp. 121–126 (1986).

Leonardi, A., et al., "Synthesis Pharmacological Evaluation and Structure–Activity Relationship and Quantitative Structure–Activity Relationship Studies on Novel Derivatives of 2,4–diamino–6,7–dimethoxyquinazoline $\alpha_1$–Adrenoceptor Anagonists", J. Medicinal Chemistry, 42:427–437 (1999).

Leonardi, A., et al; "Pharmacological Characterization of the Uroselective Alpha–1 Antagonist Rec 15/2739 (SB 216469): Role of the Alpha–IL Adrenoceptor in Tissue Selectivity, Part 1"; vol. 281, No. 3; *J. of Pharmacology and Experimental Therapeutics;* pp. 1272–1283 (1997).

Lomasney, Jon W., et al; "Mammalian $\alpha_1$_Adrenergic Receptor: Purification and Characterization of the Native Receptor Ligand Binding Subunit"; *J. of Biological Chemistry;* vol. 261, No. 17; pp. 7710–7716 (1986).

Lomasney, Jon W.; et al; "Molecular Cloning and Expression of the cDNA for the $\alpha_{1A}$–Adrenergic Receptor:The Gene for Which is Located on Human Chromosome 5"; *J. of Biological Chemistry;* vol. 266, No. 10; pp. 6365–6369 (1991).

Maniatis, T. et al; "Rapid Isolation of Plasmid or Bacteriophage λ DNA", *Cold Spring Harbor Laboratory/Molecular Cloning, A Laboratory Manual;* pp. 365–370 (1982).

Min, Kweonski, et al., "Functional Activity of Alpha–Adrenergic Receptors in Rabbit Vagina", Abstract, *Boston Female Sexual Function Conference*—Oct. 26–27, 2000.

Montorsi, Francesco; "Pharmacological Management of Erectile Dysfunction"; *Practical Therapeutics; Drugs* vol. 50(3): pp. 465–479 (1995).

Muramatsu, Ikunobu, et al; "Functional Subclassification of Vascular $\alpha_1$–Adrenoceptors"; *Pharmacology Communications;* vol. 6; Nos. 1–3; pp. 23–28 (1995).

Oshita, Masafumi et al; "Pharmacological Characterization of Two Distinct $\alpha_1$–Adrenoceptor Subtypes In Rabbit Thoracic Aorta", *J. Pharmacol.* vol. 108, pp. 1071–1076 (1993).

Park, K.; "Vasculogenic Female Sexual Dysfunction:The Hemodynamic Basis for Vaginal Engorgement Insufficiency and Clitoral Erectile Insufficiency"; *Int. J. of Impotence Research;* vol. 9; pp. 27–37 (1997).

Peterson, Craig, A.; Erectile Response To Transurethral Alprostadil, Prazosin and Alprostadil–Trazosin Combinations; *J. of Urology;* vol. 159; pp. 1523–1528 (May 1998).

Robert, JMH, et al; "Non–carboxylic Antiinflammatory Compounds. III. N–(4,6–Dimethylpyridin–2–yl)arylcarboxamides and Arylthiocarboxamides Acting as Brain Edema Inhibitors"; *Eur. J. Med Chem;* vol. 30: pp. 915–924 (1995).

Goepel, Mark, et al., "Characterization of α–Adrenoceptor Subtypes in the Corpus Cavernosum of Patients Undergoing Sex Change Surgery"; J. Urology, 162(5)1793–1799 (1999).

Giuliano, Francois et al; "Antierectile Role of the Sympathetic Nervous System In Rats"; *J. of Urology;* vol. 150, pp. 519–524 (Aug. 1993).

Harrison's Principles of Internal Medicine, 14th ed., p. 10, (1998).

Hatzichristou, DG; "Current Treatment and Future Perspectives For Erectile Dysfunction"; *Int. J. of Impotence Research;* vol. 10, Suppl. 1, pp. S3–S13 (1998).

Hayashida, Hideshi; "Comparison of Neurogenic Contraction and Relaxation in Canine Corpus Cavernosum and Penile Artery and Vein"; *Jpn. J. Pharmacol.;* vol. 72, pp. 231–240 (1996).

Hedlund, H, et al; "Comparison of the Responses to Drugs Acting on Adrenoreceptors and Muscarinic Receptors in Human Isolated Corpus Cavernosum and Cavernous Artery"; *J. Auton. Pharmcol.;* vol. 5; pp. 81–88 (1985).

Hieble, Paul, J.; International Union of Pharmacology X. Recommendation for Nomenclature of $\alpha_1$_Adrenoceptors:Consensus Update; *Pharmacological Reviews;* vol. 47; No. 2; pp. 267–270, (c) 1995).

Holmquist, Fredrik, et al; Effects of the $\alpha_1$–Adrenoceptor Antagonist R–(—)–YM12617 on Isolated Human Penile Erectile Tissue and Vas Deferens; *Eur.J. of Pharmacol.;* vol. 186; pp. 87–93 (1990).

Israel, Manisha, "Viagra: The First Oral Treatment for Impotence", Pharmaceutical Journal, Pharmaceutical Society, London, GB, 261:164–165 (1998).

Johnson, William S., et al; "An Approach To Taxodione Involving Biomimetic Polyene Cyclization Methodology"; *Tetrahedron,* vol. 38. No. 10; pp. 1397–1404 (1982).

Kawasaki, Ernest S., et al; "Detection of Gene Expression"; in *PCR Technology: Principles and Applications for DNA Amplification,* H.A. Erlich (ed.); pp. 89–97 (1989).

Kobilka, Brian K., et al; "cDNA For the Human $\beta_2$–Adrenergic Receptor: A Protein With Multiple Membrane–Spanning Domains and Encoded By a Gene Whose Chromosomal Location Is Shared With That of the Receptor for Platelet–Derived Growth Factor"; *Proc. Natl. Acad. Sci;* vol. 84, pp. 46–50 (Jan. 1987).

Cotecchia, Susanna, L.M.; "Phorbol Ester Effects on $\alpha_1$ Adrenoceptor Binding and Phosphatidylinositol Metabolism In Cultured Vascular Smooth Muscle Cells"; *Life Sciences,* vol. 37, pp. 2389–2398 (1985).

Cotecchia, Susanna, et al; Molecular Cloning and Expression of the cDNA for the Hamster $\alpha_1$–Adrenergic Receptor; *Proc. Natl. Acad. Sci;* vol. 85; pp. 7159–7163 (Oct. 1988).

Cullen, Bryan R.; "Use of Eukaryotic Expression Technology in The Functional Analysis of Cloned Genes", *Methods In Enzymology,* vol. 152; pp. 684–704, (c) 1987.

Davis, B.J., et al; "Adrenoceptor Subtypes in Human Penile Tissue"; Br. J. Pharmacol; vol. 125; p. 13 (1998).

DeLean, A., et al; "Simultaneous Analysis of Families of Sigmoidal Curves:Application To Bioassay, Radioligand Assay, And Physiological Dose–Response Curves"; *Am. J. Physiol,* vol. 235(2); pp. E97–E102 (1978).

DeLean, Andre, et al; "Validation and Statistical Analysis of a Computer Modeling Method for Quantitative Analysis of Radioligand Binding Data for Mixtures of Pharmacological Receptor Subtypes", *the American Society for Pharmacology and Experimental Therapeutics,* vol. 21; pp. 5–16 (1982).

DeLean, A., et al; "Simultaneous Analysis of Families of Sigmoidal Curves:Application To Bioassay, Radioligand Assay, And Physiological Dose–Response Curves"; *Am. J. Physiol,* vol. 235(2); pp. E97–E102 (1978).

Dixon, Richard A.F., et al; "Cloning of the Gene and cDNA for Mammalian β–Adrenergic Receptor and Homology With Rhodopsin"; *Letters to Nature;* vol. 321, pp. 75–79 (May 1986).

Docherty, James R; "Subtypes of Functional $\alpha_1$_and $\alpha_2$–Adrenoceptors"; *European J. of Pharmacol.;* vol. 361, pp. 1–15 (1998).

Feldman, Henry A; "Impotence and Its Medical and Psychosocial Correlates:Results of the Massachusetts Male Aging Study"; *J.of Urology;* vol. 151; pp. 54–61 (Jan. 1994).

Flavahan, N.A., et al.; "$\alpha_1$-Adrenoceptor Subclassification in Vascular Smooth Muscle"; *TIPS;* pp. 347–349 (Sep. 1986).

Giardian, Dario, et al; "Synthesis and Biological Profile of the Enantiomers of [4-(4-Amino-6,7-dimethoxy-quinazoline-2-yl)-cis-octahydroquinoxalin-1-yl]furan-2-ylmethanone (Cyclazosin), a Potent Competitive $\alpha_{1B}$-Adrenoceptor Antagonist"; *J. Med. Chem;* vol. 39; pp. 4601–4607 (1996).

Giardinà, Dario., et al., "Structure–Activity Relationships in Prazosin–Related Compounds. 2.[1] Role of the Piperazine Ring on $\alpha$–Blocking Activity[2]", J. Medicinal Chemistry, 36:690–698 (1993).

Askin, David et al; "Highly Diastereoselective Reaction of a Chiral, Non–Racemic Amide Enolate With (S)–Glycidyl Tosylate. Synthesis of the Orally Active HIV–1, Protease Inhibitor L–735,524"; *Tetrahedron Letters,* vol. 35, No. 5, pp. 673–676 (1994).

Aviv, Haim, et al; "Purification of Biologically Active Globin Messenger RNA by Chromatography On Oligothymidylic Acid–Cellulose"; *Proc. Natl. Acad. Sci;* vol. 69, No. 6; pp. 1408–1412 (Jun. 1972).

Boolell, Mitradev, et al., "Sildenafil: An Orally Active Type 5 Cyclic GMP–Specific Phosphodiesterase Inhibitor for the Treatment of Penile Erectile Dysfunction", International Journal of Impotence Research, Stockton, Basingstoke, GB, 8:47–52 (1996).

Brill, Earl, et al; "Quinoxaline Studies. XI. Unequivocal Syntheses of Cis–and Trans–dl–Decahydroquinoxalines. Resolution of Trans–dl–Decahydroquinoxalines[1–3]"; *J. of Org. Chemistry;* vol. 29; pp. 1135–1138 (1963).

Brill, Earl, et al; "Quinoxaline Studies. XII. Stereodirective Syntheses of Cis–and Trans–Decahydroquinoxalines and cis–and trans–Decahydroquinoxalines–2[1,2]"; *J. of Org. Chemistry;* vol. 29; pp. 579–581 (1964).

Brindley, G.S., et al; "Pilot Experiments on the Actions of Drugs Injected Into the Human Corpus Cavernosum Penis"; *Br. J. Pharmac;* vol. 87; pp. 495–500 (1986).

Carati, C. J., et al; "Autonomic Control of Penile Erection In The Dog"; *J. Physiol;* vol. 384; pp. 524–538 (1987).

Cheng, Yung–Chi; "Relationship Between The Inhibition Constant ($K_1$) and The Concentration of Inhibitor Which Causes 50 Per Cent Inhibition ($I_{50}$) of An Enzymatic Reaction"; *Biochemical Pharmacology,* vol. 22, pp. 3099–3108 (1973).

Chirgwin, John M., et al; "Isolation of Biologically Active Ribonucleic Acid From Sources Enriched In Ribonuclease", *The American Chemical Society;* vol. 18, No. 24; pp. 5294–5299 (1979).

Christ, George J; "Pharmacological Studies of Human Erectile Tissue:Characteristics of Spontaneous Contractions and Alternations in $\alpha$–adrenoceptor Responsiveness With Age and Disease in Isolated Tissues"; *Br. J. Pharmacol;* vol. 101; pp. 375–381 (1990).

Collins, Sheila, et al; "$\beta_2$–Adrenergic Receptors In Hamster Smooth Muscle Cells are Transcriptionally Regulated by Glucocorticoids"; *J. of Biological Chemistry;* vol. 263, No. 19; pp. 9067–9070 (1988).

Cornett, Lawrence E., et al; "Characterization of The $\alpha_1$–Adrenoceptor Subtype In A Smooth Muscle Cell Line"*J. of Biological Chemistry,* vol. 257, No. 2, pp. 694–697, (1982).

Anderson, Karl–Erik; "Pharmacology of Lower Urinary Tract Smooth Muscles and Penile Erectile Tissues"; *Pharmacological Reviews;* vol. 45, No. 3; pp. 253–308, (c) (1993).

Andersson, Stefan, et al; "Cloning, Structure, and Expression of the Mitochondrial Cytochrome P–450 Sterol 26–Hydroxylase, A Bile Acid Biosynthetic Enzyme"; *J. of Biological Chemistry;* vol. 264, No. 14; pp. 8222–8229 (1989).

Arunlakshana, O., et al; "Some Quantitative Uses of Drug Antagonists"; *Brit. J. Pharmacol;* pp. 48–58 (1959).

Fig. 1

Fig. 2

USE OF SELECTIVE ANTAGONISTS OF THE $\alpha_{1B}$-ADRENERGIC RECEPTOR FOR IMPROVEMENT OF SEXUAL DYSFUNCTION This is a continuation, of application Ser. No. 09/565,842, filed May 5, 2000 (now U.S. Pat. No. 6,303,606) which claims priority of Provisional Patent Application Serial No. 60/183,257, filed Feb. 17, 2000 under 35 U.S.C. § 119(e) and of Italian Patent Application MI 99A000995, filed May 7, 1999 under 35 U.S.C. § 119(a)–(d). Each of these prior applications is hereby incorporated herein by reference, in its entirety.

FIELD OF THE INVENTION

This invention relates to the use in the treatment of human sexual dysfunction of selective antagonists of the $\alpha_{1B}$-adrenergic receptor and to pharmaceutical compositions containing them as compounds for assisting the sexual act.

BACKGROUND OF THE INVENTION

Sexual dysfunction is the result of different mechanisms in males and females. In males impotence is defined as the inability to obtain an erection sufficient for intercourse. Erection is achieved as a result of blood inflow into the corpora cavernosa of the penis, which produces engorgement of the corpora cavernosa, and subsequent penile erection. It is estimated that as many as 30 million American men experience some degree of erectile dysfunction, the prevalence of which increases with age (Feldman et al., *J. Urol.* 151: 54–61, 1994).

The causes of impotence can be divided into two subcategories: 1) organic and 2) psychological. The organic aspects of impotence are caused by underlying vascular disease such as that associated with hypertension, diabetes mellitus and prescription medications. About half of all cases of impotence are of vascular origin. Because the physiologic process of erection is initiated by an increase in blood flow through the penile arteries and shunting of blood into the vascular spaces of the corpora cavernosa, erectile dysfunction can result from the inability of the arteries of the penis to dilate, thereby inhibiting the flow of blood into the erectile tissue.

The sympathetic pathways play a primary role in the neural control of penile erection. It is generally accepted that, in the detumescent state, release of noradrenaline (NA), acting on postjunctional $\alpha_1$-receptors on the cavernous arteries and on the corpora cavernosa (Christ et al., *Br. J. Pharmacol.* 101: 375–381, 1990), contributes to keep the penile smooth muscle contracted. Conversely, intracavernous injection of $a_1$-antagonists like phenoxybenzamine, phentolamine and moxisylyte produced tumescence and erection (see for review Andersson K. -E, *Pharmacol. Rev.* 45: 253–308, 1993; Montorsi et al., *Drugs* 50: 465–479, 1995; Hatzichristou D. G., *Int. J. Impot. Res.* 10: S3–S13, 1998).

The erectile response to transurethral prazosin in human males has been recently reported (Peterson et al., *J. Urol.* 159: 1527–1528, 1998) as well as the relaxing effect of this antagonist on human male, dog and rat isolated penile tissues and vessels (Hedlund and Andersson, *J Auton. Pharmacol.* 5: 81–88, 1985; Holmquist et al., *Eur. J. Pharmacol* 186: 87–93, 1990; Hayashida et al., *Jpn. J. Pharmacol.* 72: 231–240, 1996).

In females the sexual response initiates with a stimulation which causes vasocongestion and results in lubrication of the vagina in preparation for penis insertion. Lubrication is due to formation of an exudate which, together with genital congestion, produces the so-called orgasmic platform which preludes to orgasm. In brief, female sexual dysfunction may be due to interference with the different stages of intercourse and can be related to either organic or functional causes, or both.

Several reasons including stress, anxiety, depression, fatigue, interpersonal conflicts between the partners or more simply ageing, can lead to failure of the vasocongestive response, thereby inhibiting normal vaginal lubrication. Women in this condition may be incapable of achieving a normal sexual response without appropriate treatments (Harrisons' *Principles of Internal Medicine*, 14$^{th}$ Ed., page 291, McGraw-Hill (1998)). It has been recently confirmed that both vaginal vasocongestion and clitoral erection depend on increased blood flow (Park K. et al., *Int. J. Impot. Res.* 9, 27–37 (1997)).

Moreover, similarly to what reported for the male sexual organ, the same authors demonstrated that a local injection in the vagina of $\alpha_1$-adrenergic antagonists such as phentolamine can increase blood flow and intravaginal pressure up to levels comparable with those achieved by stimulation of the pelvic nerve. These data clearly indicate that noradrenaline plays an important role in maintaining flaccidity of the organ concerned in the female sexual tract too.

It is thus important to identify new products having an $\alpha_1$-adrenoceptor antagonistic activity, which can be useful in promoting vasodilatation of the arteries in the vaginal walls and clitoris, thereby improving lubrication and helping continuation of the sexual act.

Pharmacological, biochemical and radioligand binding studies evidenced three different $\alpha_1$-receptor subtypes with a high affinity for prazosin, namely $\alpha_{1A}$-($\alpha_{1a}$-), $\alpha_{1B}$-($\alpha_{1b}$-) and $\alpha_{1D}$-($\alpha_{1d}$-), with lower case subscripts being used for recombinant receptors and upper case subscripts for receptors in native tissues (Hieble et al., *Pharmacol. Rev.* 47: 267–270, 1995). In functional studies $\alpha_1$-receptors with a low affinity for prazosin have also been identified and termed $\alpha_{1L}$-receptors (Flavahan et al., *Trends Pharmacol. Sci.* 7: 347–349, 1986; Muramatsu et al., *Pharmacol. Comm.* 6: 23–28, 1995).

Several studies have demonstrated the presence of these $\alpha_1$-adrenergic receptor subtypes in the animal and human cavernous tissues. By using in situ hybridization with specific oligonucleotide probes and protection assays techniques (Traish, A., et al., *J. Urol.* 153: 222–227, 1995; Traish, A., et al., Receptor 5: 145–157, 1995; Véronneau-Longueville et al., *Int. J. Impot. Res.* 10: 187–194, 1998) demonstrated that human and rat corpus cavernosum tissues expressed all three cloned $\alpha_1$-adrenergic receptor subtypes.

On the other hand, functional studies in male human penile tissue are controversial, suggesting the involvement of all three cloned $\alpha_1$-ADR subtypes (Traish et al. *J. Urol.* 153: 222–227, 1995), or that the $\alpha_{1L}$-ADR subtype is the main mediator of NA-induced contraction in this tissue (Davids et al. *Br. J. Pharmacol.* 125: 13P, 1998). Conversely, nothing is known so far about vaginal vessels.

Pharmacological evidence for the univocal presence of a well defined $\alpha_1$-adrenergic receptor subtype(s) in the penile or vaginal tissue would represent a major advance in the field of male and female sexual dysfunction treatment, allowing the possibility of the use of selective $\alpha_1$-antagonists.

The $\alpha$-antagonists currently being used for the treatment of predominantly male impotence suffer from unwanted side effects, such as priapism, a painful erection of exceeding long duration which may result in fibrosis of cavernous tissue (Brindley et al., Br. J. Pharmacol 87, 495–500, 1986). Other side effects are penile pain and hypotension (Peterson et al. J. Urol. 159: 1523–1527, 1998).

Thus there is still a need for selective $\alpha_1$-antagonists which do not subject the impotent patient to the side effects of known treatments, notably of the cardiovascular type.

Accordingly, it is a primary object of the present invention to provide a method of treating impotence, both male and female, which avoids any excessive side effects due to acute hypotension.

It is another object of the present invention to provide pharmaceutical compositions comprising selective $\alpha_{1b}$-adrenoceptor antagonists, which compositions are effective for the treatment of male erectile impotence and female sexual dysfunction.

It is another object of the present invention to provide a method of treating sexual dysfunction using selective $\alpha_{1b}$-adrenoceptor antagonists.

Other features and advantages of the present invention will be apparent to those of skill in the art from the following detailed description and appended claims.

SUMMARY OF THE INVENTION

The present invention is directed to a method of treating sexual dysfunction. The method comprises administering an amount of selective $\alpha_{1b}$-adrenoceptor antagonists or pharmaceutically acceptable salts thereof, sufficient to treat such sexual dysfunction.

The selective antagonists which are an object of the invention have the following chemical structure I:

wherein:

B is selected from a group consisting of a heterocyclic amine of formula:

and A represents a 2-furyl, (substituted) 2-furyl, 2-tetrahydrofuryl, substituted alkoxy or substituted phenoxyalkyl group, their pharmaceutically acceptable salts and single enantiomers or diastereoisomers, with the proviso that when B is $B_1$ then A must be substituted phenoxyalkyl.

In another aspect, the present invention provides methods for treating male erectile impotence and female sexual dysfunction that involve administering to affected mammals effective amounts of a compound that:

a) binds to mammalian $\alpha_{1b}$ adrenergic receptors with an affinity ($K_i$) of at least about $10^{-8}$ M;
b) binds to mammalian $\alpha_{1b}$ adrenergic receptors with an affinity at least 10 fold higher than the affinity with which the compound binds to mammalian $\alpha_{1a}$ or $\alpha_{1d}$ or $\alpha_{1L}$ adrenergic receptors.

The methods for ascertaining whether these criteria are met are discussed below.

The present invention is also directed to pharmaceutical compositions comprising selective $\alpha_{1b}$-adrenoceptor antagonists and pharmaceutically acceptable carriers for administration in accordance with such methods.

In a preferred embodiment, selective $\alpha_{1b}$-adrenoceptor antagonists are administered to a patient in an amount between 0.1 mg/dose and 10.0 mg/dose at a time immediately preceding sexual engagement. Selective $\alpha_{1b}$-adrenoceptor antagonists are preferably administered through intracavernous injection or by the intraurethral or transdermal route in males or intravaginal route in females.

In yet another aspect, the invention provides a method for identifying a compound useful for treating sexual dysfunction. The method is carried out using the steps of:

a) individually measuring the binding affinity of test compounds for a mammalian $\alpha_{1b}$ adrenergic receptor and a mammalian $\alpha_{1a}$ or $\alpha_{1d}$ adrenergic receptor by radioreceptor binding techniques;
b) measuring the affinity for a mammalian $\alpha_{1L}$-adrenergic receptor by antagonising the contractile effect of an a, adrenergic receptor agonist on selected mammalian tissue;
c) identifying those compounds that
  1) bind to an $\alpha_{1b}$-adrenergic receptor with an affinity (Ki) of at least $10^{-8}$ M;
  2) bind to an $\alpha_{1b}$-adrenergic receptor with an affinity at least 10 fold stronger than the affinity which the compound has for the $\alpha_{1a}$, $\alpha_{1d}$ and $\alpha_{1L}$ adrenergic receptors.

Preferably, the activity of the compounds identified in step (c) above is confirmed by evaluating its effect in increasing the intracavernous pressure in the rat or in the dog, and blood flow in the vaginal wall and clitoris in the rabbit.

BRIEF DESCRIPTION OF THE FIGURES

The following figures are illustrative of embodiments of the invention and are not meant to limit the scope of the invention as encompassed by the claims.

Data represent the mean values of the ratio. The basal (background) value is represented by the first bar; the vehicle: $2^{nd}$ bar; different tested doses: other bars (Compound A: 10, 30, 100 and 300 µg; prazosin and phentolamine: 10, 30, 100, 300 and 1000 µg). The percent decreases of mean BP evaluated versus the basal values reported in Tables 3–5 are also shown. Compound A increased the ICP/BP ratio in a dose-dependent manner. Increases higher than 40% were obtained in presence of decreases of blood pressure not exceeding 20%. On the contrary, the increases of ICP/BP induced by prazosin and phentolamine were poorly dose-dependent and both compounds induced, at the same doses, marked hypotension, defined as the decrease of blood pressure equal to or higher than 40% compared to the premedication level.

Data represent the mean values of the ratio. Basal: first bar; different tested doses: other bars (Compound A: 3, 10, 30, 100 and 300 µg; Compound B: 3, 30, 100, 300 and 1000 µg; prazosin: 30, 100, 300 and 1000 µg; phentolamine: 10, 30, 100, 300 and 1000 µg). The percent decreases of DBP evaluated versus the basal values reported in Table 6–9 are also shown.

Compound A increased the ICP/BP ratio in a dose-dependent manner. Increases higher than 80% were obtained in presence of decreases of blood pressure not exceeding 20%. Similar results were obtained after administration of Compound B. On the contrary, the increases of ICP/BP induced by prazosin were lower than those obtained after Compounds A and B, and this reference compound induced a marked hypotension. Phentolamine increased the ICP/BP ratio only after the administration of the highest dose.

DETAILED DESCRIPTION OF THE INVENTION

All patents, patent applications, and references cited herein are hereby incorporated by reference in their entirety. In the case of inconsistency between the explicit disclosure of the present application and any material incorporated by reference, the present disclosure, including the definitions, will control.

The present invention provides methods and compositions for treating sexual dysfunction. The methods involve administering to affected individuals selective antagonists of the $\alpha_{1b}$ adrenergic receptor at an appropriate time and in an amount effective for facilitating penile erection or vaginal vasocongestion.

Antagonists of the $\alpha_{1b}$ adrenergic receptor suitable for use in practising the present invention include without limitation those compounds having the following properties:

1) Potency: useful compounds preferably exhibit a radioreceptor binding affinity of $1.10^{-8}$ M or lower for mammalian $\alpha_{1b}$ adrenergic receptors.
2) Selectivity: preferred compounds exhibit at least 10-fold lower affinity for mammalian $\alpha_{1a}$, $\alpha_{1d}$ and $\alpha_{1L}$ adrenergic receptors.

Screening candidate compounds to identify those that are useful in practising the present invention involves measuring the specific binding activity of the compounds towards different neuronal a, adrenergic receptors (such as $\alpha_{1a}$, $\alpha_{1b}$ and $\alpha_{1d}$ subtypes according to the method of Testa et al., *Pharmacol. Comm.* 6: 79–86, 1995), that may be achieved by using any of a multiplicity of methods that are well-known in the art, such as, for example, competitive binding to native or cloned receptors.

Typically, a biological source of, for example $\alpha_{1b}$ adrenergic receptors is used in which the receptor is present at a sufficiently high concentration so that binding of a labelled ligand is easily measurable. This source may comprise a mammalian tissue or fluid (either in situ or after removal from the animal) or a tissue culture cell. The target receptor may be expressed from either an endogenous (native) gene or from a transfected receptor-encoding recombinant gene. For example the rat liver is a rich (native) source of $\alpha_{1B}$ adrenergic receptors (Taddei et al., *Life Sci.* 53: PL177–PL181, 1993). Alternatively hamster U1b adrenergic receptor cDNA can be transiently expressed in COS-7 cells in culture (Cotecchia S. et al., *Proc. Natl. Acad. Sci. USA* 85: 7159–7163, 1988) and human $\alpha_{1b}$ adrenergic receptor cDNA can be expressed in CHO cells in culture (Testa et al., *Pharmacol. Comm.* 6: 79–86, 1995).

Furthermore, human $\alpha_{1a}$ and $\alpha_{1d}$ adrenergic receptor cDNA has been expressed in CHO cells (Testa et al., *Pharmacol. Comm.* 6: 79–86, 1995, with details described in Taddei C. et al., *Life Sci.* 53: 177–181, 1993; and Testa R. et al., *Europ. J. Pharmacol.* 249: 307–315, 1993) whereas bovine $\alpha_{1a}$ (formerly $\alpha_{1c}$) (Schwinn et al., *J Biol. Chem.* 265: 8183–8189, 1990) and rat $\alpha_{1d}$ (Lomasney et al., *J. Biol. Chem.* 266: 6365–6369, 1991) clones of the adrenergic receptor have been transiently expressed in COS-7 cells and can be used to assess selectivity for the $\alpha_{1b}$ adrenergic receptor by a radioreceptor binding technique. These techniques are employed in the present examples. Details of the aforementioned protocols can be performed as described in Schwinn D. A. et al., *J. Biol. Chem.* 265: 8181–8189, 1990; Maniatis T. et al., (1982) *Molecular Cloning: A Laboratory Manual*, pp. 365–370, Cold Spring Harbor Laboratory, Cold Spring Harbor, N.Y.; Anderson S. et al., *J. Biol. Chem.* 264: 8222–8229, 1989; Cullen B. R., *Methods Enzymol.* 152: 684–704, 1975; Viera J. et al., *Gene (Amst)*, 19: 259–268, 1982; Sanger F. et al., *Proc. Natl. Acad. Sci. USA*, 74: 5463–5476, 1977; Chirgwin J. M. et al., *Biochemistry* 18: 5294–5299, 1979; DeLean A. et al., *Mol. Pharmacol.* 21: 5–16, 1982; Yang-Feng T. L. et al., *Cytogenet. Cell Genet.*, 43:121–126, 1986; Dixon R. et al., *Nature (London)* 321: 75–79, 1986; Cornett L. E., et al., *J. Biol. Chem.* 257: 694–697, 1982; Lomasney J. W. et al., *J. Biol. Chem.* 261: 7710–7716, 1986; Cotecchia S. et al., *Life Sci.* 37: 2389–2398, 1986; Kobilka B. K., *Proc. Natl. Acad. Sci. USA* 84: 46–50, 1987; Aviv H. et al., *Proc. Natl. Acad. Sci. USA* 69: 1408–1412; Collins S. et al., *J. Biol. Chem.* 263: 9067–9070; 1988; Kawasaki E. S. et al., A.M. (1989) in *PCR Technology Principles and Applications for DNA Amplification* (Erlich, H. A. ed) Stockton Press, New York.

The ability of the test compounds to compete with the appropriate labelled ligand for receptor binding is then measured and a binding constant (Ki) is calculated using the Cheng and Prusoff equation (Cheng et al., *Biochem Pharmacol.* 22: 3099–3108, 1973) or equivalent computational method well known in the art.

A detailed description of receptor binding experiments is given in Example 8 below. Although the affinity and selectivity values given above are not intended to be tied to any particular experimental procedure, the procedure of Example 8 is particularly preferred. However, any test for determining affinity and selectivity for the relevant receptors known in the art can be used instead.

On the contrary, no radioreceptor binding techniques are available for determining the affinity of compounds for the $\alpha_{1L}$ adrenergic receptor subtype, even though this subtype can be studied by functional techniques in a variety of tissues, such as rabbit mesenteric and carotid arteries, rat vas deferens and small mesenteric artery, human prostate (see for review Doherty J. R. *Eur. J. Pharmacol.* 361: 1–15, 1998), as well as rabbit aorta pretreated with chloroethyl-clonidine (Testa et al., *J. Pharmacol. Exp. Ther.* 281: 1284–1293, 1997) The latter Testa et al. method was used in the examples below to evaluate the functional $\alpha_1$-antagonistic activity of compounds. Further details for such technique can be found in Leonardi A. et al. patents, Italian Patent MI92A000408, U.S. Pat. Nos. 5,403,842, 5,474,994, 5,605,897; Leonardi A. et al., *J. Pharmacol. Exp. Ther.* 281: 1272–1283, 1997; Oshita M. et al., *J. Pharmacol.* 108: 1071–1076, 1993; Testa R. et al., *Eur. J. Pharmacol.* 249: 307–315, 1993; Testa R. et al., *Pharmacol. Commun.* 6: 79–86, 1995).

In this approach, the ability of the test compounds to inhibit the NA-induced contraction of the tissues is measured and the dissociation constant (Kb) is estimated (Arunlakshana et al., *Br. J. Pharmacol. Chemother.* 14: 45–58, 1959), or equivalent computational method well known in the art. A detailed description is given in Example 9 below, which again is preferred but not intended to limit the methodology of the present invention.

As discussed above the compounds useful in practising the present invention bind to the $\alpha_{1b}$ adrenergic receptor with an affinity (Ki) of at least $10^{-8}$ M and have an affinity for the $\alpha_{a1}$, $\alpha_{1b}$ and $\alpha_{1L}$ adrenergic receptors at least 10-fold lower.

Once a compound is identified as possessing the above characteristics, its pharmacological activity can be confirmed using one or more animal model systems for studying male erection. Useful animal model systems include without limitation, increase of intracavernous pressure in anesthetized rats and/or dogs.

In such methods, compounds are administered into corpus cavernosum and the intracavernous pressure developed is measured, simultaneously to blood pressure. The efficacy of the compounds is better measured by evaluating the ratio between intracavernous and blood pressure, which are strictly correlated.

In this way an activity index is obtained which is expressed as a percent value and reflects the percent of ICP with respect to blood pressure, which can reach a maximum value of 100%. These methods are described in detail in Examples 10 and 11 below. (The comment expressed above about the nonlimitative character of these methods applies to the methods of Examples 10 and 11 as well.)

As measured using the above in vivo models, useful compounds induce a significant increase with regard to vehicle in the ICP/BP ratio when administered locally at a dose of 10–1000 μg with a blood pressure decrease lower than 20% (30% only at the highest dosage).

A model to measure the effects of the products of the invention on vaginal and clitoral pressure is described in Example 12, again not intended to limit the methodology that can be used in connection with the invention.

Examples of selective $\alpha_{1b}$ adrenergic receptor antagonists for use in the present invention include the following quinazoline derivatives of formula I:

wherein:

B is selected from a group consisting of a heterocyclic amine of formula:

and A represents a 2-furyl, (substituted) 2-furyl, 2-tetrahydrofuryl, substituted alkoxy or substituted phenoxyalkyl group, their pharmaceutically acceptable salts and single enantiomers or diastereoisomers, with the proviso that when B is $B_1$ then A must be substituted phenoxyalkyl.

The term "substituted" in the foregoing includes without limitation: one or more groups chosen from the group consisting of hydrogen, halo, hydroxyl, cyano, nitro, amino, alkylamino, alkyl, alkenyl, alkynyl, alkoxy, aryl, aryloxy carboxy, heteroaryl, heterocyclic, cycloalkyl, trifluoromethyl, thio, amido.

The preferred compounds are those where $B_2$ is represented by the (S)-enantiomer of formula II:

$B_3$ has a cis stereochemistry, with the junctional hydrogen atoms having the same orientation:

and A = with $R_1$ and $R_2$ being alkyl or alkoxy groups; the most preferred compounds are those where $B_1$ and $B_2$ have the same meanings as above and $B_3$ has the following stereochemistry:

and A= with $R_1$=linear or branched $C_{1-5}$ alkyl and $R_2=C_{1-4}$ alkoxy.

Methods of preparation of the quinazoline derivatives of formula I are disclosed in the following references: WO 95/25726; Giardina D. et al., J. Med. Chem. 39, 4602–7 (1996); WO 97/11698.

The preferred compounds of formula I include:

4-amino-6,7-dimethoxy-2-[4-[(2-isopropyl6-methoxyphenoxy)acetyl]-1-piperazinyl]quinazoline (Compound A)

4-amino-6,7-dimethoxy-2-[(4aR,8aS)-4-(2-furoyl)-cis-octahydro-1-quinoxalinyl]quinazoline (Compound B)

4-amino-6,7-dimethoxy-2-[3(S)-3-(t-butylcarbamoyl)-4-(2-furoyl)-1-piperazinyl] quinazoline (Compound C)

The synthesis of the compounds of formula I can be performed according to the following scheme (wherein A and B have the meaning given above and X is halogen or hydroxy):

The starting material 1 is commercially available (e.g. from Lancaster Synthesis Ltd, Eastgate, White Lund, Morecambe, Lancashire, LA3 3DY, England) or alternatively can be prepared as described by Althuis et al., J. Med. Chem. 20, 146–149 (1977). The amines H-B-H can be in the form of the racemate or homochiral where appropriate and can be commercially available, such as piperazine, or can be prepared according to methods described in the literature. For example, amine can be prepared as described by Brill et al., J. Org. Chem. 28, 1135–1138 (1963) or by stereoselective synthesis as described by Brill et al., J. Org. Chem. 29, 579–581 (1964), and amine can be prepared starting from 2-pyrazinecarboxylic acid (available, e.g., from Aldrich Chemical Co., Milwaukee, Wis.) by amidification followed by reduction and resolution as described in Tet. Lett. 35, 673–676 (1994). The reaction is performed at 150–200° C. without solvent or in the presence of a suitable polar solvent, such as 1-amyl alcohol or n-butyl alcohol, at reflux temperature.

Intermediates ACOX are commercially available or can be prepared, when A=phenoxyalkyl, starting from the corresponding phenol derivative, by reaction with a haloalkyl carboxylic acid ester, followed by hydrolysis and chlorination, by the methods known to those skilled in the art and described in Example 1 for The condensation to give I may be carried out by reaction of intermediate 2 with ACOX, where X represents a halogen atom (e.g. chlorine), in a chlorinated solvent, such as chloroform or methylene chloride, or in an aprotic polar solvent, such as dimethylformamide, in the presence of a base, such as triethylamine or diisopropylamine, at 0° C. to 40° C. Alternatively, when X represents a hydroxyl group the condensation may be carried out in a chlorinated or aprotic polar solvent as above reported, in the presence of a condensing agent, such as dicyclohexylcarbodiimide, and of a promoting agent, such as 4-dimethylaminopyridine at a temperature of 0° C. to 40°C., or other equivalent.

Alternatively, the following scheme can be used:

The suitable acyl chlorides are reacted with HBH compounds in polar solvents such as dimethylformamide, acetone or acetonitrile, optionally in the presence of a base such as potassium or cesium carbonate or triethylamine, at 20–100° C.

The intermediates AC(O)BH are then reacted with intermediate 1 to give compounds I. This alkylation may be carried out in a polar protic solvent such as i-amyl alcohol and n-butyl alcohol or in an aprotic solvent such as dimethylformamide, at 60° C. to reflux.

The enantiomers of compounds I in which B is $B_2$ may be obtained starting from the suitable $HB_2H$ enantiomers, that are obtained by salification of the racemate with an optically active acid, such as (S)-10-camphorsulphonic acid in a suitable solvent or solvent mixture, followed by separation of the diastereomeric salts by recrystallisation.

Similarly, the enantiomers of compounds I in which B is $B_3$ may be obtained by salification of the racemic intermediate 2 with a suitable optically active acid followed by diastereomeric separation.

Further preferred is a compound having the general Formula III wherein A is chosen from the group consisting of a substituted 2-furyl-2-tetrahydrofuryl, substituted alkoxy and substituted phenoxyalkyl group or an enantiomer, diastereomer or pharmaceutically acceptable salt of such a compound. Further preferred is a compound according to formula III wherein the octahydroquinoxaline ring has the (4aR, 8aS) configuration. Further preferred is a compound in which A represents a group of the formula wherein $R_1$ represents a linear or branched alkyl chain having from 1 to 5 carbon atoms and $R_2$ represents an alkoxy group having from 1 to 4 carbon atoms.

Further preferred is a compound of Formula III, wherein A is chosen from a group consisting of 5-methyl-2-furyl, 2-tetrahydrofuryl, benzyloxy and 2-isopropyl-6-methoxyphenoxymethyl.

Representative selective antagonists is when in compound I $B=B_3$ and A=substituted phenoxy alkyl.

Representative also is when in compound I $B=B_2$ and A=substituted phenoxy alkyl.

Representative also is when in compound I $B=B_3$ and A=substituted 2-furyl.

Representative also is when in compound I $B=B_2$ and A=substituted 2-furyl.

Representative also is when in compound I $B=B_3$ and A=2 tetrahydrofuryl.

Representative also is when $B=B_2$ and A=unsubstituted furyl.

Representative also is when $B=B_2$ and A=substituted alkoxy.

Representative also is when compound I $B=B_2$ and A=2 tetrahydrofuryl and pharmaceutically acceptable salts and single enantiomers or diastereoisomers of the foregoing.

Further representative examples of the compounds of the invention are with no intention to limit are 4 amino-6,7dimethoxy-2-[(4aR,8aS)-4-(2-5 methoxy furoyl)acetyl-cis-octahydro-1-quinoxalinyl] quinazoline 4 amino-6,7dimethoxy-2-[(3S)-3-(t-butylcarbamoyl)-4-(2-isopropyl-6-methoxy phenoxy acetyl-1-piperazinyl) quinazoline 4 amino-6,7dimethoxy-2-[(4aR,8aS)-4-(2-methyl-6 methoxy phenoxy acetyl)-cis octahydro-1-quinoxalinyl]quinazoline 4 amino-6,7dimethoxy-2-[(3S)-3-(t-butylcarbamoyl)-4-(5 methoxy furoyl) acetyl-1-piperazinyl)quinazoline 4 amino-6,7dimethoxy-2-[(4aR,8aS)-4-2-(5 methoxy tetrahydrofuroyl) acetyl-cis-octahydro-1-quinoxalinyl] quinazoline 4 amino-6,7dimethoxy-2-[(3S)-3-(t-butylcarbamoyl)-4-2-(5 methoxy tetrahydrofuroyl) acetyl-1-piperazinyl) quinazoline Therapeutic Applications The present invention encompasses the pharmaceutical formulations comprising the $\alpha_{1b}$ adrenergic receptor antagonists listed above, as well as the methods employing these formulations for treating male and female sexual dysfunction, in particular that due to vascular origin.

The neural sympathetic control appears to maintain the penis and the vaginal wall, as well as the clitoris, in their flaccid state, and antagonising the effect of sympathetic mediators in these tissues with selective $\alpha_{1b}$ adrenergic receptor antagonists allows this negative control to be overcome. The result is relaxation of the penile smooth muscle and vasodilatation of the cavernous arteries in the male and vasocongestion in the female. In the male, blood flow into the trabecular spaces of the corpora cavernosa is increased, causing engorgement of the penis (tumescence). Expansion of the trabecular walls against the tunica albuginea compresses subtunical venules and impedes venous outflow, resulting in sustained tumescence, i.e. an erection. In females, vasocongestion allows vaginal lubrication thus makes it a satisfactory sexual activity possible.

An "effective amount" of the compound for treating sexual dysfunction is an amount that results in measurable amelioration of erection as assessed by the increase of the intracavernous pressure In the male, an additional parameter is the duration of erection, while in the female the effective amount is that which produces a measurable increase in the amount of blood flow in the clitoris and vaginal wall. This measurement can be made by laser doppler fluorimetry and is well known to one of ordinary skill in the art.

The effective dosage range for treating sexual dysfunction can be determined by experimentation using methods known in the art, such as by establishing a matrix of dosages and frequencies and comparing a group of experimental units or subjects at each point in the matrix. The exact amount to be administered to a patient may vary depending on the state and severity of the disorder and the physical condition of the patient. A measurable amelioration of any symptom or parameter may be determined by a physician skilled in the art or reported by the patient to the physician. It will be understood that any significant clinical or statistical improvement is within the scope of this invention. Clinically significant improvement is defined as an improvement perceptible to the patient and or to the physician.

Preferably, the compounds of the present invention are employed in combination with a suitable pharmaceutical carrier prior to administration. Such compositions comprise a therapeutically effective amount of the compound of the invention and a pharmaceutically acceptable carrier or excipient. For example, when administration is by injection, an aqueous solution acceptable by intracavernosal injection into the penis is prepared. In this instance, the carriers include but are not limited to water, saline, buffered saline, salts, glycerol and ethanol, either alone or in combination. Also, a non-irritant preservative such as, for example, benzalkonium chloride may be added to the compositions.

In the case of intraurethral, subcutaneous or topical administration, the pharmaceutical carrier includes but is not limited to gels such as petroleum gels, ointments, creams, solutions, sprays, powders, foams and liposome formulations. The carrier is water-soluble, non-irritating, and does not sensitise the skin. In a preferred embodiment, the carrier for this type of administration has a semi-soft cream-like consistency. This can be obtained by the use of a hydrogel such as hydroxypropylmethylcellulose.

For intravaginal administration in a vaginal douche, carriers include but are not limited to water, saline, buffered saline, salts, glycerol and ethanol, either alone or in combination. Moreover, a non-irritating preservative including, for example, benzalkonium chloride may be added to the compositions.

The carriers for administration in a cream or vaginal ovule include but are not limited to propylene glycol, hydrogenated lanolin, sweet almond oil, polyglycol esters of fatty acids, cetyl alcohol, glyceryl monostearate, sodium edetate, triglycerides of fatty acids, gelatine, glycerine, titanium dioxide, parabens.

The pharmaceutical compositions comprising the compounds of the invention may optionally comprise other active agents which enhance or complement the sexual-act improving effects of the compounds of the invention. Such active agents include, but are not limited to, prostaglandins, for example prostaglandin $E_2$; direct vasodilators, for example papaverine; and type-V phosphodiesterase inhibitors, for example 1-{[3-(4,7-dihydro-1-methyl-7-oxo-3-propyl-1H-pyrazolo[3,4-d]pyrimidin-5-yl-4-ethoxyphenyl]-4-methylpiperazine also known as sildenafil. These compounds supplement the direct action of the compounds of the invention in producing the desired amelioration effects.

The use of a compound according to the present invention in conjunction with sildenafil may also allow the dosage of the latter to be reduced, minimizing its undesirable side effects by administering the combination orally or intravenously or also by one of the methods discussed in the next paragraphs. As used herein, "in conjunction" with means to achieve the desired result of treating sexual dysfunction at the same time. For example, the compounds of the present invention could be administered, e.g., intracavernously immediately prior to intercourse whereas the subject would have already taken sildenafil orally prior to administration of the compound of the invention. It is anticipated that sildenafil administration will typically occur 30 to 60 minutes prior to administration of the compound of the invention.

Preferably, the compounds of the invention are administered according to one of following methods. The compounds of the invention may be administered by injection wherein the compounds of the invention are dissolved in saline at a concentration ranging from 0.2 to 20 mg/ml. A volume of 0.5 ml is injected intracavernously. In another example of a preferred method of use, the compounds of the invention are formulated in a petrolatum gel, which is then applied externally to an intraurethral catheter which is used to deliver the composition. The dosage of the compounds of the invention is in the range of 1 to 10 percent of the weight of composition applied. The catheter is inserted into the urethra in order to administer the compounds of the invention intraurethrally and to produce the vasodilatation required for erection. Sildenafil may be co-administered.

Any amount of the above described compounds which is effective in relieving human sexual dysfunction may be administered by injection. A range of about 0.1 to 10 mg/dose is used in a single dose. Preferably about 0.3 mg/dose to about 3 mg/dose is used in a single dose taken 0–60 minutes prior to intercourse.

For a vaginal douche, concentration may range from 0.2% to 5%, while for a vaginal cream concentration may range from 1% to 10%. The amount which can be administered by means of a vaginal ovule may range from 1 to 100 mg. 15 to 60 minutes prior to intercourse.

The methods, tables and examples provided below are intended to more fully describe the preferred embodiments of the invention and to demonstrate its advantages and applicability without limiting its scope.

EXAMPLE 1

4-Amino-6,7-dimethoxy-2-[4-[(2-isopropyl-6-methoxyphenoxy)acetyl]-1-piperazinyl]quinazoline hydrochloride (I: A=2-isopropyl-6-methoxyphenoxymethyl, B=$B_1$)

(Compound A)

2-Methoxy-6-isopropylphenoxyacetic Acid (Intermediate 1A)

A solution of 11.1 ml of ethyl bromoacetate in 10 ml of toluene was added dropwise at room temperature over about 15 minutes into a mixture of 20 g of NaOH, 30 ml of $H_2O$, 1.1 g of triethylbenzylammonium chloride, 8.4 g of 2-isopropyl-6-methoxyphenol (prepared according to Johnson et al., *Tetrahedron.* 38, 1397–1404 (1982)) and 40 ml of toluene. The mixture was stirred vigorously at the same temperature for 2 h and thereafter for 2 h at 60–65° C. and for 6.5 h under reflux. During this last step a solution of 6 ml of ethyl bromoacetate in 10 ml of toluene was added. In the end the mixture was diluted with 250 ml of $H_2O$. The aqueous phase was separated off and treated with concentrated HCl; the emulsified precipitate was extracted with $Et_2O$ (3×50 ml) and the organic phase was washed with water. Another extraction was performed with 40 ml of 20% $Na_2CO_3$ and the slightly alkaline solution was treated with concentrated HCl and extracted with $Et_2O$ (3×40 ml). The extracts were pooled and the solvent was evaporated off, giving 8 g (72%) of the desired compound; b.p. 190° C./0.7 mmHg.

4-Amino-6,7-dimethoxy-2-[4-[(2-isopropyl-6-methoxyphenoxy)acetyl]-1-piperazinyl-quinazoline hydrochloride 3.6 ml of $SOCl_2$ were added dropwise into a boiling solution of 6 g of intermediate 1A in 30 ml of $CCl_4$ and the mixture was stirred under reflux for 2 h. The oily residue, obtained by evaporation of the reaction mixture, was dissolved in 26 ml of $CHCl_3$ and the solution was added dropwise over 30 minutes into a stirred solution of 7.75 g of 4-amino-6,7-dimethoxy-2-(1-piperazinyl)quinazoline and 4.1 ml of $Et_3N$ in 50 ml of DMF. After stirring for 2 hours, the solvents were evaporated off to dryness. The residue was dissolved in 250 ml of $CHCl_3$. The solution was washed with 2.5% $NaHCO_3$ and then with $H_2O$, and finally evaporated to dryness. The purification was performed by column chromatography using $CHCl_3$/MeOH 100:3 as eluting mixture. The residue was suspended into 100 ml of boiling ethanol, and ethanolic HCl was then added in a slight excess until dissolved. After cooling, the hydrochloride salt was collected by suction and recrystallized from ethanol to give 6.4 g (45%) of the product; m.p. 252–254° C.

EXAMPLE 2

4-Amino-6,7-dimethoxy-2-[(4aR,8aS)-4-(2-furoyl)-cis-octahydro-1-quinoxalinyl]-quinazoline hydrochloride (I: A=(2-furyl), B=$B_3$) (Compound B)

(±)-(2-furoyl)-cis-octahydroquinoxaline (2A)

1.44 g of 48% hydrobromic acid was added dropwise to a solution of 3.85 g of cis-octahydroquinoxaline (prepared as described in Brill et al., *J. Org. Chem.* 28, 1135–1138, (1963)) in 26 ml of ethanol and 4 ml of $H_2O$ stirred at 40–45° C. 1.16 g of 2-furoyl chloride was added dropwise over 15 minutes into the resulting solution and stirring was continued for 3 h at 80° C. The solution was concentrated to low volume, diluted with water and extracted with chloroform. The residue obtained after solvent evaporation was purified by flash chromatography eluting with petroleum ether: ethyl acetate: methanol: 28% aqueous ammonia 8:6:2:0.2 to give 2.35 g (40%) of the desired compound. M.p. 178° C. dec.

(+)-1-(2-furoyl)-cis-octahydroquinoxaline (2B)

A solution of 2.35 g of the above intermediate 2A in 22 ml of methanol was treated with a solution of 1.54 g of (S)-(+)-mandelic acid in 22 ml of methanol. The mixture was evaporated to dryness to give a residue which was crystallized by dissolving the solid in 265 ml of hot ethyl acetate and then reducing the volume by evaporation to about 130 ml. The precipitate was recrystallized another six times with the same solvent to give 0.4 g of the (+)-mandelate salt; m.p. 188–190° C., $[\alpha]^{20}_D$=+79.4° (c=1, MeOH). The salt was dissolved in water, the ice-cooled solution made basic with 2N NaOH, and the resulting mixture extracted with chloroform (3×22 ml). Removal of the dried solvent gave 0.21 g of the desired compound as a waxy solid; m.p. 47–50° C., $[\alpha]^{20}_D$=+70.1° (c=1, MeOH).

4-Amino-6,7-dimethoxy-2-[(4aR,8aS)-4-(2-furoyl)-cis-octahydro-1-quinoxalinyl]-quinazoline hydrochloride A mixture of 0.21 g of the above intermediate 2B, 0.18 g of 4-amino-2-chloro-6,7-dimethoxyquinazoline and 0.2 g of N,N-diisopropylethylamine in 13 ml of isoamyl alcohol was heated at reflux for 72 h. After cooling, the mixture was left at 0° C. overnight. The solid was then collected, triturated with cold 2N NaOH, filtered, washed with water, and transformed into the hydrochloride salt. Crystallization from MeOH/15% EtOH gave 0.06 g of the title compound. M.p. 262–264° C., $[\alpha]^{20}_D$=+74.4° (c=1, MeOH).

EXAMPLE 3

4-Amino-6,7-dimethoxy-2-[(3S)-3-(t-butylcarbamoyl)-4-(2-furoyl)-1-piperazinyl]-quinazoline (I: A=2-furyl, B=$B_2$) (Compound C)

4-Amino-6,7-dimethoxy-2-r(3S)-3-(t-butylcarbamoyl)-1-piperazinyl]quinazoline (3A)

A mixture of 0.36 g of 4-amino-2-chloro-6,7-dimethoxyquinazoline, 1.08 g of (S)-N-tert-butyl-2-piperazinecarboxamide bis-(1 S)-(+)-10-camphorsulfonate, prepared as described in U.S. Pat. No. 5,700,364, and 0.94 ml of diisopropylethylamine in 10 ml of isoamyl alcohol was heated at reflux for 9 h. After cooling to room temperature, the solvent was evaporated in vacuo and 50 ml of dichloromethane was added to the residue. The mixture was washed with water (3×20 ml), 5% aqueous $Na_2CO_3$ (30 ml), water (3×20 ml), dried ($Na_2SO_4$) and evaporated to dryness. The residue was purified by flash chromatography eluting with chloroform: 2N methanolic ammonia 100:3 to give 0.173 g (30%) of the desired compound. $^1$H-NMR ($CDCl_3$, δ): 1.35 (s, 9H, $C(CH_3)_3$), 1.65–2.10 (m, 1H, piperazine NH), 2.30–3.40 (m, 5H, piperazine CHs), 3.95 (s, 6H, $OCH_3$), 4.45 (d, 1H, piperazine CH), 4.68 (dd, 1H, piperazine CH), 6.00–6.45 (m, 2H, $NH_2$), 6.85–7.10 (m, 2H, CONH and quinazoline H8), 7.18 (s, 1H, quinazoline H5).

4-Amino-6,7-dimethoxy-2-[(3S)-3-(t-butylcarbamoyl)-4-(2-furoyl)-1-piperazinyl]-quinazoline A mixture of 0.243 g of the above intermediate 3A, 0.17 ml of diisopropylethylamine, 0.08 ml of 2-furoyl chloride in 10 ml of dichloromethane was stirred at room temperature for 10 hours. The solution was diluted with dichloromethane (10 ml), washed with water (4×10 ml), 2N NaOH (4×10 ml), water (4×10 ml), dried ($Na_2SO_4$) and evaporated to dryness. The residue was purified by flash chromatography eluting with petroleum ether:ethyl acetate 100:2 to give 0.2 g (68%) of the title compound as an ivory solid.

$^1$H-NMR (DMSO-$d_6$, δ): 1.14 (s, 9H, $C(CH_3)_3$), 3.08–3.22 (m, 1H, piperazine CH), 3.32–3.47 (m, 2H, piperazine CHs), 3.77 (s, 3H, $OCH_3$), 3.81 (s, 3H, $OCH_3$), 4.10–4.25 (m, 1H, piperazine CH), 4.35–4.50 (m, 1H, piperazine CH), 4.82–4.98 (m, 2H, piperazine CHs), 6.61–6.66 (m, 1H, furan H4), 6.69 (s, 1H, furan H3), 6.95–7.18 (m, 3H, CONH and $NH_2$), 7.42 (s, 1H, quinoline H8), 7.55 (s, 1H, quinoline H5), 7.85 (s,1H, furan H5).

EXAMPLE 4

4-Amino-6,7-dimethoxy-2-[(±)-4-(2-isopropyl-6-methoxyphenoxyacetyl)-cis-octahydro-1-quinoxalinyl] quinazoline hydrochloride.2.5$H_2O$ (I: A=2-methoxy-6-isopropylphenoxymethyl, B=$B_3$)

4-Amino-6,7-dimethoxy-2-[(±)-cis-octahydro-1-quinoxalinyl]-quinazoline dihydrochloride.2.5$H_2O$ (4A)

A mixture of 7.85 g of 4-amino-2-chloro-6,7-dimethoxyquinazoline, 13.3 g of triethylamine, 0.4 g of dimethylaminopyridine, 11.5 g of cis-decahydroquinoxaline and 80 ml of i-amyl alcohol was stirred at reflux for 72 hours. After cooling to room temperature, the solvent was evaporated off and the residue was purified by flash chromatography, eluting with petroleum ether:ethyl acetate: methanol:28% ammonium hydroxide 8:6:2:0.2. The obtained residue obtained was transformed into the hydrochloride salt and crystallized from i-propanol/methanol 1:1 to give 14.7 g (73%) of the desired compound; m.p. 290–295° C.

4-Amino-6,7-dimethoxy-2-[4-chloroacetyl-(±)-cis-octahydro-1-quinoxalinyl]-quinazoline hydrochloride (4B)

A solution of 0.26 g of chloroacetyl chloride in 6 ml of methylene chloride was added dropwise over 15 minutes at 0° C. to a stirred mixture of 0.5 g of the above intermediate 4A and 0.21 g of diisopropylethylamine in 15 ml of methylene chloride. After 4-hour stirring at room temperature and 72-hour resting in a refrigerator, the solid was collected by suction and purified by crystallisation from chloroform to give 0.12 g (33%) of the desired product; m.p. >270° C.

$^1$H-NMR (CDCl$_3$, δ): 1.30–2.35 (m, 8H, octahydroquinoxaline CHs at position 5, 6, 7 and 8), 3.70–4.18 (m, 10H, octahydroquinoxaline CHs at position 2 and 3 and 2 OCH$_3$), 4.20–4.36 (m, 1H, octahydroquinoxaline H4a), 4.47 (s, 2H, CH$_2$Cl), 4.60–4.78 (m, 1H, octahydroquinoxaline H8a), 7.48 (s, 1H, quinoline H8), 7.75 (s, 1H, quinoline H5), 8.66 (br, 1H, NH), 8.90 (br, 1H, NH), 11.95 (br, 1H, NH).

4-Amino-6,7-dimethoxy-2-[(±)-4-(2-isopropyl-6-methoxyphenoxyacetyl)-cis-octahydro-1-quinoxalinyl]quinazoline hydrochloride.2.5H$_2$O 10 ml of a freshly prepared 0.095M EtONa solution was added to a stirred solution of 0.16 g of 2-isopropyl-6-methoxyphenol in 5 ml of ethanol and stirring was continued for 0.5 hours at room temperature. The resulting solution was added dropwise in 15 minutes into a stirred solution 0.2 g of the above intermediate 4B in 50 ml of ethanol under nitrogen atmosphere. The mixture was stirred for 5 hours at room temperature and was then refluxed for 20 hours. The residue obtained after solvent evaporation was converted into the hydrochloride salt and crystallized from i-propanol to give 0.64 g (21%) of the title compound; m.p. 208–209° C.

EXAMPLE 5

4-Amino-6,7-dimethoxy-2-[(±)-4-(5-methyl-2-furoyl)-cis-octahydro-1-quinoxalinyl]-quinazoline hydrochloride.2.5H$_2$O (I: A=-(5-methyl-2-furyl), B=B$_3$)

5-Methyl-2-furoyl chloride (5A)

A solution of 0.31 g of SOCl$_2$ in 2 ml of benzene was added dropwise at 0° C. under nitrogen atmosphere to a solution of 0.22 g of 5-methylfuran-2-carboxylic acid, prepared following the method described by Robert et al., *Eur. J. Med. Chem.* 30, 915–924 (1995), in 5 ml of benzene. The mixture was stirred at 80° C. for 1 hour and the excess SOCl$_2$ was then distilled off. The residue (0.24 g, 97% of theory) was utilized for the next step without further purification.

4-Amino-6,7-dimethoxy-2-](±)-4-(5-methyl-2-furoyl)-cis-octahydro-1-quinoxalinyl]-quinazoline hydrochloride.2.5H$_2$O A solution of 0.24 g of the above intermediate 5A in 5 ml of methylene chloride was added dropwise at 0° C. to a stirred solution of 0.56 g of intermediate 4A and 0.25 g of triethylamine in 10 ml of methylene chloride. The mixture was stirred at room temperature for 3 hours and then kept at 0–4° C. overnight. The precipitate was collected by suction and purified by flash chromatography eluting with petroleum ether:ethyl acetate:methanol:28% ammonium hydroxide 8:8:2:0.2. The pure base was transformed into the hydrochloride salt from i-propanol to give 0.2 g (27%) of the title compound; m.p. 268–270° C.

EXAMPLE 6

4-Amino-6,7-dimethoxy-2-[(±)-4-(2-tetrahydrofuroyl)-cis-octahydro-1-quinoxalinyl]quinazoline hydrochloride.2.5H$_2$O (I: A=(2-tetrahydrofuryl), B=B$_3$)

2-Tetrahydrofuroyl chloride (6A)

A mixture of 0.22 g of 2-tetrahydrofuroic acid and 0.5 ml of SOCl$_2$ in 10 ml of benzene was stirred at 80° C. for 1 hour. The excess of SOCl$_2$ and benzene were distilled off to give 0.25 g of an oily residue which was considered 80% pure and was used for the next step without further purification.

4-Amino-6,7-dimethoxy-2-[(±)4-(2-tetrahydrofuroyl)-cis-octahydro-1-quinoxalinyl]-quinazoline hydrochloride.2.5H$_2$O This compound was prepared according to the method described for the compound in Example 5, but using the above intermediate 6A instead of intermediate 5A and performing a flash chromatography eluting with petroleum ether:ethyl acetate:methanol:14% ammonium hydroxide at a ratio of 8:6:2:0.1. The pure base was transformed into the hydrochloride salt and crystallized from ethanol to give 21% of the title compound; m.p. 220–223° C.

EXAMPLE 7

4-Amino-6,7-dimethoxy-2-[(±)-4-benzyloxycarbonyl-cis-octahydro-1-quinoxalinyl]-quinazoline hydrochloride.0.75H$_2$O (I: A=benzyloxy, B=B$_3$)

This compound was prepared according to the method described for the compounds in Example 5, but using benzyloxycarbonyl chloride instead of intermediate 5A and the flash chromatography was carried out eluting with petroleum ether:ethyl acetate:methanol:14% ammonium hydroxide 8:5:0.6:0.025. The pure base was transformed into the hydrochloride salt and crystallized from ethanol to give 14% of the title compound; m.p. 243–245° C.

EXAMPLE 8

Radioligand Binding Assay at Cloned α$_1$-adrenoceptors.

[$^3$H]Prazosin binding to bovine α$_{1a}$, hamster α$_{1b}$ and rat α$_{1d}$-adrenoceptors was performed in COS-7 cell (CV-1 monkey kidney epithelial cells) membranes expressing transiently bovine α$_{1a}$, hamster α$_{1b}$ and rat α$_{1d}$-adrenoceptors. Construction and transfection of individual α$_1$-adrenoceptors were carried out as previously described (Schwinn et al., *J. Biol. Chem.* 265: 8183–8189, 1990; Cotecchia S. et al., *Proc. Natl. Acad. Sci. USA* 85: 7159–7163, 1988; Lomasney et al., *J. Biol. Chem.* 266: 6365–6369, 1991).

COS-7 cell membranes (35, 35 and 70 μg protein/sample for α$_{1b}$, α$_{1a}$ and α$_{1d}$, respectively) were incubated in 50 mM Tris, pH 7.4, containing 10 μM of pargyline and 0.1% of ascorbic acid, with 1.1 nM [$^3$H]prazosin, in a final volume of 0.22 ml, for 30 minutes at 25° C., in the absence or presence of competing drugs (1 pM–10 μM). Non-specific binding was determined in the presence of 100 μM of phentolamine.

The incubation was stopped by addition of ice-cold Tris buffer and rapid filtration through 0.2% polyethyleneimine pretreated Whatman GF/B or Schleicher & Schuell GF52 filters.

Binding to cloned human α$_1$-adrenoceptor subtypes was performed in membranes from CHO cells (Chinese hamster ovary cells) transfected by electroporation with DNA expressing the gene encoding each α$_1$-adrenoceptor subtype. Cloning and stable expression of the human α$_1$-adrenoceptor gene was performed as previously described (Testa et al., *Pharmacol. Comm.* 6: 79–86, 1995)

and the following CHO cell membranes (30 μg of proteins) were incubated in 50 mM of Tris, pH 7.4, with 0.2 nM of [$^3$H]prazosin in a final volume of 1.02 ml for 30 min at 25° C., in the absence or presence of competing drugs (1 pM–10 μM). Non-specific binding was determined in the presence of 10 μM of phentolamine. The incubation was stopped by addition of ice-cold Tris buffer and rapid filtration through 0.2% polyethyleneimine-pretreated Whatman GF/B or Schleicher & Schuell GF52 filters.

The inhibition of specific binding of the radioligand by the tested drugs was analyzed to estimate the $IC_{50}$ value by using a non-linear curve-fitting program (De Lean et al., A. J. Physiol. 235: E97–E102, 1978). The $IC_{50}$ value was converted to an affinity constant (Ki) by the equation of Cheng & Prusoff (Cheng et al., Biochem. Pharmacol. 22: 3099–3108, 1973). Data are expressed as mean Ki. All patents and other references cited herein are incorporated by reference in their entirety.

Results

The compounds of Examples 1 to 7 exhibited the desired potency at $\alpha_{1b}$-adrenoceptor, their Ki (affinity) values being higher than $1 \times 10^{-8}$ M (Table 1).

Compound A, Compound B and Compound C were also selective for the $a_{1b}$-adrenoceptor, their affinity for the other $\alpha_1$-subtypes being at least 10-fold lower.

TABLE 1

Affinity (Ki, nM) of the different compounds tested for animal and human recombinant $\alpha_1$-adrenoceptor subtypes

| | Animal cloned receptors | | | Human cloned receptors | | |
|---|---|---|---|---|---|---|
| | $\alpha_{1a}$ | $\alpha_{1b}$ | $\alpha_{1d}$ | $\alpha_{1a}$ | $\alpha_{1b}$ | $\alpha_{1d}$ |
| Example 1 - Compound A | 7.5 | 0.45 | 10.34 | — | — | — |
| Example 2 - Compound B | 32.94 | 0.68 | 26.9 | 9.43 | 0.17 | 2.63 |
| Example 3 - Compound C | — | — | — | 94.12 | 1.76 | 25.07 |
| Example 4 | — | — | — | — | 0.16 | — |
| Example 5 | — | — | — | — | 0.24 | — |
| Example 7 | — | — | — | — | 0.65 | — |
| Prazosin | 0.72 | 0.46 | 1.39 | 0.61 | 0.42 | 0.23 |
| Phentolamine | 3.22 | 89.15 | 67.05 | 4.8 | 33.21 | 17.26 |

EXAMPLE 9

Functional Affinity for $\alpha_{1L}$-Adrenergic Receptors

The functional $\alpha_1$-antagonistic activity of the tested compounds against noradrenaline-induced contractions of rabbit aorta pretreated with chloroethylclonidine (receptor $\alpha_{1L}$) was evaluated according to the method of Testa (Testa et al., J. Pharmacol. Exp. Ther. 281: 1284–1293, 1997). Adult male New Zealand rabbits were sacrificed by cervical dislocation. The aorta was removed, placed in Krebs-Henseleit buffer and dissected free of adhering tissue. Rings were prepared from each aorta (8 rings per aorta, about 4–5 mm wide) and suspended in 20 ml organ baths containing Krebs bicarbonate buffer of the following composition (mM): NaCl 112.0, KCl 5.0, $CaCl_2$ 2.5, $KH_2PO_4$ 1.0, $MgSO_4$ 1.2, $NaHCO_3$ 12.0 and glucose 11.1, equilibrated at 37° C. with 95% $O_2$:5% $CO_2$. Desmethylimipramine (0.1 μM) and corticosterone (1 μM) to block neuronal and extraneuronal uptake of NA, (±)-propranolol (1 μM) to block β adrenoceptors and yohimbine (0.1 μM) to block $\alpha_2$-adrenoceptors, were added to the buffer. The tissues were subject to a passive load of 2 g and the developed tension was measured using isometric transducers (Basile 7003).

The preparations were allowed to equilibrate for 60 min and then 10 μM of NA was added every 30 minutes for three times. The aortic rings were then incubated with the alkylating agent chloroethylclonidine ($5 \times 10^{-5}$ M) for 30 minutes and then washed extensively three times (in 0.5 hours) before constructing the NA concentration-response curve. After washout of NA and re-equilibration of the tissue (45 minutes), the drug to be tested was added and, after 30 minutes, a second NA cumulative concentration-response curve constructed. Each antagonist concentration was tested using 2–3 aortic rings from different rabbits.

Dose ratios (i.e. the ratio between the concentrations of noradrenaline required to produce half-maximal response in the presence and in the absence of the antagonist tested) were calculated at each concentration of the compounds. The logarithm of these dose ratio −1 was plotted against the logarithm of the compound concentrations (Schild plot) to evaluate the affinity constant Kb. When only one or two concentrations of the tested compounds were utilized, the apparent Kb value was calculated using the formula: Kb=[B]/(DOSE RATIO-1), where B is the antagonist concentration.

Results

The tested compounds showed selectivity for the $\alpha_{1b}$-adrenoceptor versus the $\alpha_{1L}$-adrenoceptor. Their functional affinity for this receptor proved, in fact, at least 10-fold lower than that for the $\alpha_{1b}$-subtype (Table 2).

TABLE 2

Functional affinity of the tested compounds for $\alpha_{1L}$-adrenoceptor subtype

| | Kb, nM |
|---|---|
| Compound A - Example 1 | 631.0 |
| Compound B - Example 2 | 741.0 |
| Compound C - Example 3 | 3715.0 |
| Prazosin | 20.9 |
| Phentolamine | 251.0 |

EXAMPLE 10

Intracavernous and Blood Pressure Recording in Rats

The evaluation of the erectile properties of the different compounds tested in rats was performed according to the method of Giuliano et al. (Giuliano et al., J. Urol. 150: 519–524, 1993).

Rats were anaesthetised by an intraperitoneal injection of urethane (1.5 g/kg in sterile saline) and placed on an homeothermic blanket. Their temperature was maintained at 37° C. Rats were tracheotomized to facilitate spontaneous breathing and to prevent aspiration of saliva. A catheter filled with heparinized saline (25 IU/ml) was placed into the carotid to record mean blood pressure (BP, mmHg). The penis was desheathed and the corpora cavernosa were exposed. A 25-gauge stainless-steel needle was inserted into one corpus cavernosum to record intracavernous pressure (ICP in mmHg). The needle was attached to a catheter filled with heparinized saline (25 IU/ml). Pressure catheters were connected to pressure transducers (Model 750, Elcomatic Ltd, Glasgow, UK).

Following a resting period of 10 minutes, the compound solvent was delivered intracavernously (50 μl/injection). Then, increasing doses of one compound were injected every ten minutes by the same route. Five injections (one solvent plus four cumulative doses) were performed in each rat, and five rats were used for the study of one compound. For each injection and for each compound, mean BP averaged over the ten minutes following the injection was measured. The maximal ICP value reached during the ten-minute period following an injection was also recorded. In these experiments, all the compounds tested were dissolved and diluted in propylene glycol-Sorensen solvent. The ICP and BP values were reported as mean ±s.e. of the mean, or percent variation (±s.e.) of the basal values. The ratios (ICP/BP)*100, which correspond to the percentage of BP reached by ICP, were calculated by using the peak effect value on ICP on the mean blood pressure observed for 10 min after injection of the compounds, and reported as mean ±s.e. of the mean.

Results

The effects of Compound A, prazosin and phentolamine are summarized in Tables 3 to 5.

Compound A dose-dependently increased ICP (from 33.9 mmHg after injection of vehicle to 50.6 mmHg) and slightly decreased BP (about 30%). The ICP increase lasted several minutes, but never overlasted the ten-minute period of screening (data not shown). Prazosin was unable to elicit any ICP increase and decreased blood pressure by 41% between solvent injection and after injection of 1000 μg/kg. Phentolamine did not modify ICP up to 300 μg/kg. After injection of 1000 μg/kg it elicited a sustained intracavernous pressure increase that lasted several minutes (not exceeding 10 minutes); at this dose phentolamine decreased BP by 30%. The ICP/BP ratio, integrating the ICP increase and BP decrease, are compared in FIG. 1. Compound A increased the ratio from 31.8 following injection of the solvent to 66.4 following injection of 300 μg/kg of the compound. The increase obtained with the highest dose of prazosin reflects only the decrease in blood pressure, since ICP did not increase at all. Phentolamine induced a slight increase only at the highest dose.

Figure 1:
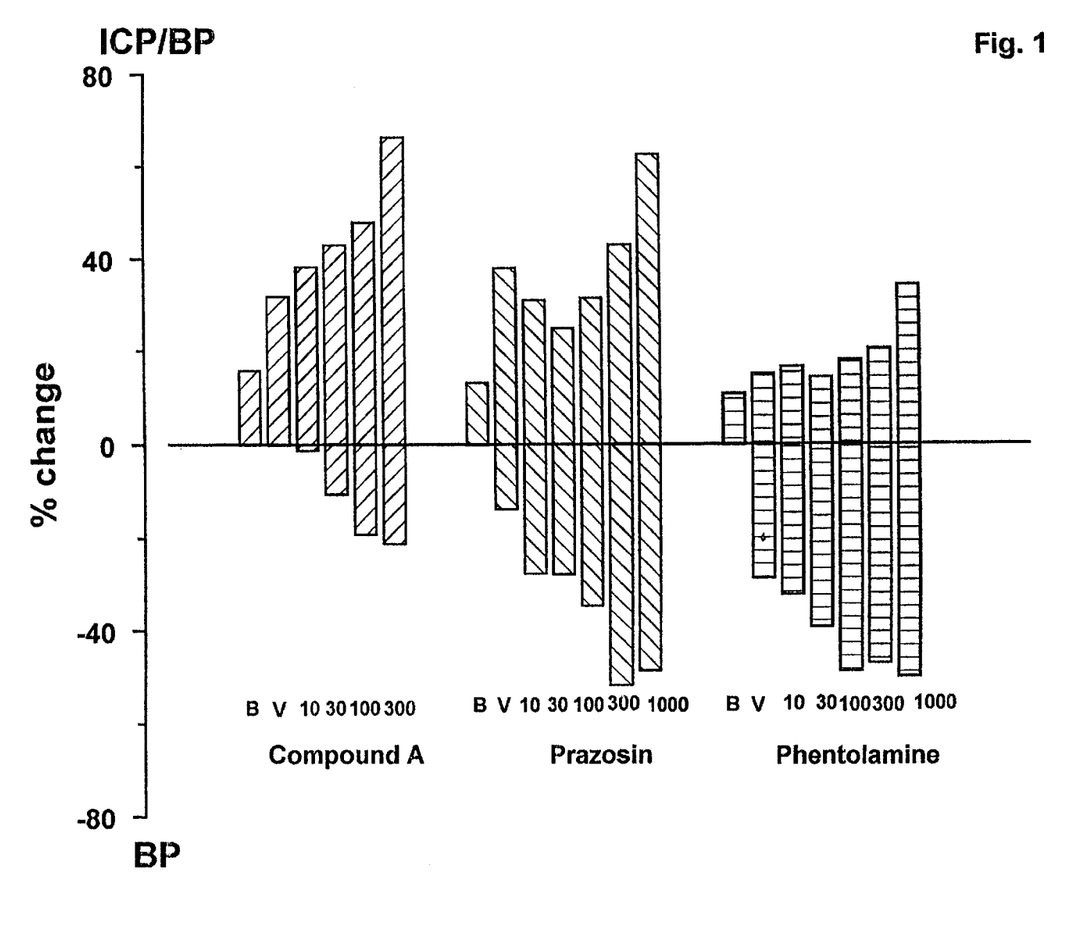
FIG. 1 is a plot showing effects of vehicle and different doses of the compounds tested on the ICP/BP ratios, corresponding to the percentage of blood pressure (BP) reached by intracavernous pressure (ICP), after intracavernous injection in rats.

The results shown in FIG. 1 clearly indicate that a dose-dependent increase of intracavernous pressure (in the absence of significant effects on blood pressure) are obtained only after administration of Compound A.

TABLE 3

Effects on intracavernous pressure and blood pressure after intracavernous injection of Compound A in anaesthetised rats (n = 5)

| Dose (μg/kg) | ICP (mmHg) | BP (mmHg) | ICP/BP Ratio |
|---|---|---|---|
| BASAL | 14.5 ± 1.6 | 92.6 ± 5.9 | 15.8 ± 1.9 |
| Vehicle | 33.9 ± 6.6 | 105.7 ± 10.1 | 31.8 ± 5.5 |
| 10 | 36.8 ± 8.7 | 91.3 ± 9.4 | 38.3 ± 5.8 |
| 30 | 37.6 ± 10.1 | 82.7 ± 11.0 | 43.0 ± 7.0 |
| 100 | 38.7 ± 12.3 | 74.8 ± 9.3 | 47.9 ± 9.2 |
| 300 | 50.6 ± 13.7 | 72.5 ± 5.6 | 66.4 ± 15.6 |

ICP = intracavernous pressure, BP = blood pressure

TABLE 4

Effects on intracavernous pressure and blood pressure after intracavernous injection of prazosin in anaesthetised rats (n = 5)

| Dose (μg/kg) | ICP (mmHg) | BP (mmHg) | ICP/BP Ratio |
|---|---|---|---|
| BASAL | 11.5 ± 2.9 | 87.5 ± 11.0 | 13.2 ± 1.3 |
| Vehicle | 26.5 ± 17.3 | 73.1 ± 9.2 | 38.0 ± 24.7 |
| 10 | 20.1 ± 6.4 | 59.4 ± 7.7 | 31.3 ± 6.2 |
| 30 | 14.9 ± 3.3 | 60.0 ± 7.4 | 24.8 ± 5.7 |
| 100 | 19.0 ± 6.6 | 56.8 ± 7.9 | 31.5 ± 8.1 |
| 300 | 18.9 ± 6.8 | 41.3 ± 3.0 | 43.0 ± 12.6 |
| 1000 | 26.9 ± 3.5 | 43.7 ± 4.1 | 62.5 ± 16.3 |

ICP = intracavernous pressure, BP = blood pressure

TABLE 5

Effects on intracavernous pressure and blood pressure after intracavernous injection of phentolamine in anaesthetised rat (n = 5)

| Dose (μg/kg) | ICP (mmHg) | BP (mmHg) | ICP/BP Ratio |
|---|---|---|---|
| BASAL | 12.9 ± 1.5 | 119.6 ± 4.2 | 10.8 ± 1.1 |
| Vehicle | 12.4 ± 1.5 | 84.6 ± 4.1 | 15.1 ± 2.5 |
| 10 | 12.6 ± 1.7 | 79.8 ± 7.3 | 16.6 ± 3.0 |
| 30 | 10.1 ± 1.4 | 72.2 ± 4.3 | 14.3 ± 2.3 |
| 100 | 10.5 ± 1.4 | 61.1 ± 7.0 | 17.9 ± 3.3 |
| 300 | 12.5 ± 2.3 | 63.0 ± 2.2 | 20.4 ± 4.4 |
| 1000 | 20.6 ± 2.1 | 59.8 ± 3.6 | 34.3 ± 2.7 |

ICP = intracavernous pressure, BP = blood pressure

EXAMPLE 11

Intracavernous and Blood Pressure Recording in Dogs

The evaluation of the erectile properties in dogs was performed according to the method of Carati (Carati et al., J. Physiol. 384: 525–538, 1987), with some modifications, as follows:

Male beagle dogs were anaesthetised with pentobarbital sodium (i.v. Nembutal, 35 mg/kg for induction and 4 mg/kg/h for maintenance) and intubated with an endotracheal cuffed tube to facilitate free ventilation. A collateral of the left femoral vein was cannulated with a PE catheter for infusion of the anaesthetic. Systemic BP was monitored via a Mikro-tip 6F (Millar Instruments) pressure transducer introduced into the aortic arch through the right common carotid artery. ICP was measured by means of a 20-gauge needle placed into the left or right corpus cavernosum and the same needle was used for intracavernous injection of the drugs. The needle was attached to a catheter filled with heparinized saline (25 IU/mL). Pressure signal was triggered by BM 614/2 amplifiers on a multichannel polygraph. The compounds to be tested were injected intracavernously in a volume of 0.5 ml and, after each injection, the needle was flushed with 0.5 ml of saline. The vehicles for compound dissolution were tested before the first dose of each drug. The compounds were administered in a cumulative way, with a 30-minute interval between doses. ICP (mmHg) was measured at the peak effect after the administration of the compounds. The duration of tumescence (DT, min) was measured from the beginning of the rise of ICP over its basal value up to the return to baseline. The systolic blood pressure and diastolic blood pressure (mmHg) were measured at the peak effect after the administration of compounds, in order to evaluate the effects of the compounds on BP independently from the effects on ICP. Moreover, the systolic blood pressure was measured at the time of maximal ICP value after intracavernous injection, to evaluate the ICP/BP ratios. In these experiments, Compound A, Compound B and phentolamine (1 or 3 mg/ml) were dissolved in 10% (v/v) N, N-dimethylformamide and further diluted in deionized $H_2O$. Prazosin was dissolved in deionized $H_2O$. The data were reported as mean ±s.e. of the mean, or percent variation (±s.e.) of the basal values.

Results

The results of the intracavernous administration of the compounds in anaesthetised dogs are reported in Tables 6 to 9. The vehicles employed for drug dilution were tested before each dose of each compound and showed no effect on either intracavernous pressure or systemic blood pressure (data not shown).

Figure 2:
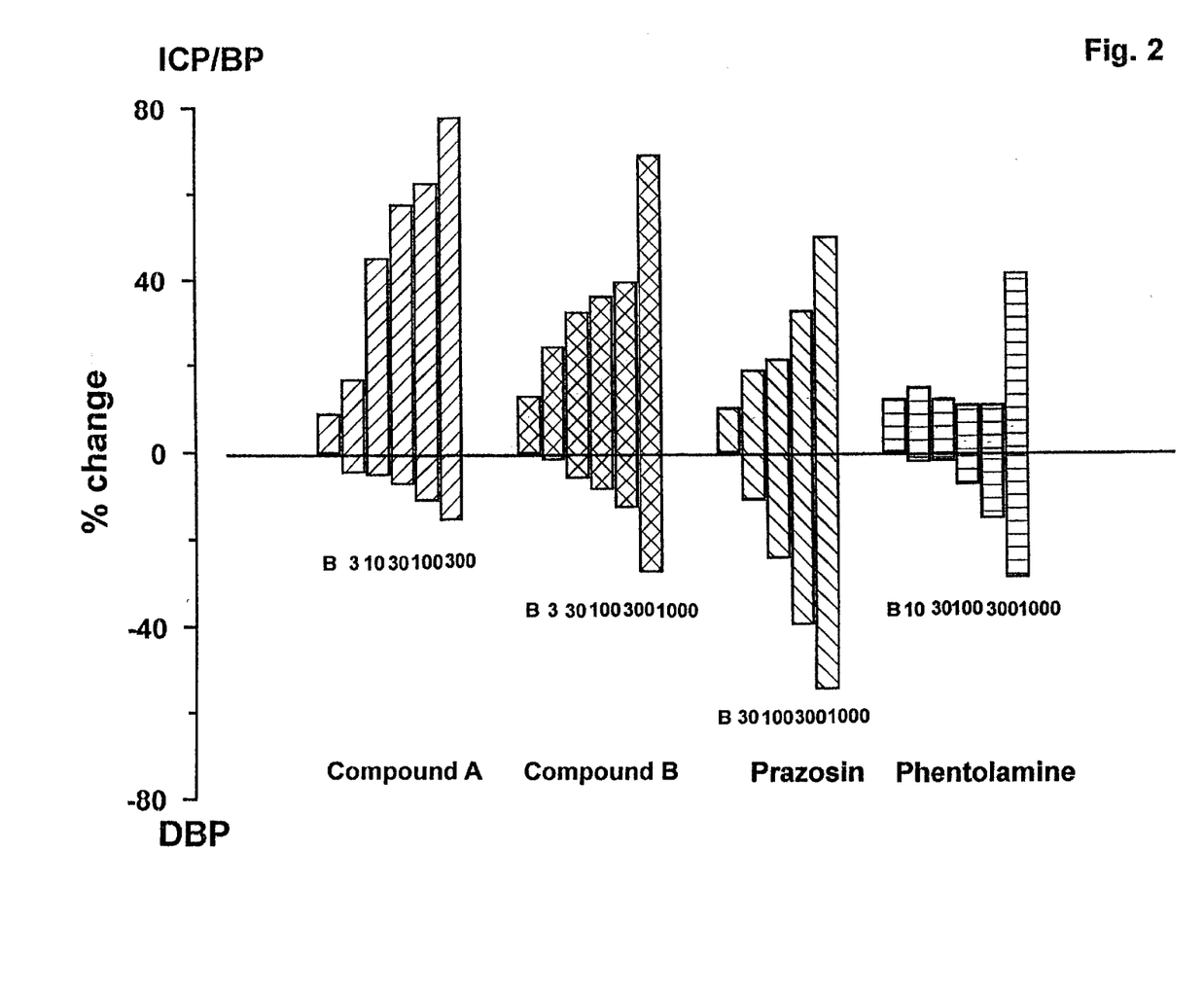
FIG. 2 is a plot showing the effects of vehicle and different doses of the compounds tested on the ICP/BP ratios, corresponding to the percentage of blood pressure (BP) reached by intracavernous pressure (ICP) after intracavernous injection in dogs.

All compounds tested induced an increase of intracavernous pressure (ICP). Compound A dose-dependently increased ICP (in comparison with basal ICP values) from 12 mmHg at 3 µg/kg to 96.5 mmHg with the highest dose (300 µg/kg). The duration of the increase of intracavernous pressure (DT), too, was dose-dependent and lasted at least 30 min at the highest dose. The compound induced a slight dose-dependent hypotension (computed on diastolic blood pressure) from −10 to −19 mmHg. Compound B increased ICP in a dose-dependent way from 13.7 mmHg (at 3 µg/kg) to 73.3 mmHg (1000 µg/kg) and induced hypotension only with the highest dose (−31 mmHg on diastolic blood pressure). DT lasted about 40 min at the highest dose. Prazosin and phentolamine increased ICP at doses that induced substained hypotension. Furthermore the ICP increase observed after injection of these reference compounds was not dose-dependent. Prazosin, at 1000 µg, induced an ICP increase of 36 mmHg only, and decreased diastolic blood pressure by 71 mmHg. Similarly, phentolamine (at the same dose) increased ICP by 43 mmHg, but decreased diastolic blood pressure by 37 mmHg. The ICP/BP ratios are reported in FIG. 2. Compound A increased the ICP/BP ratio in a dose-dependent manner. Increases higher than 80% were obtained in the presence of decreases of blood pressure not exceeding 20%. Similar results were obtained after administration of Compound B. On the contrary, the increases of ICP/BP induced by prazosin were lower than those obtained after Compounds A and B, and this reference compound induced a marked hypotension. Phentolamine increased the ICP/BP ratio only after the administration of the highest dose, which induced a relevant hypotension.

TABLE 6

Effects on intracavernous pressure and blood pressure after intracavernous injection of Compound A in anaesthetised dogs (n = 4)

| DOSE (µg/kg) | ICP (mmHg) | DT (min) | SBP (mmHg) | DBP (mmHg) | $SBP_{ICP}$ (mmHg) | ICP/BP RATIO |
|---|---|---|---|---|---|---|
| BASAL | 145 ± 2.2 | — | 163.0 ± 5.4 | 126.5 ± 5.5 | — | 8.8 ± 1.2 |
| 3 | 26.7 ± 8.7 | 1.2 ± 0.2 | 155.3 ± 5.5 | 116.0 ± 5.9 | 156.7 ± 6.8 | 16.6 ± 4.7 |
| 10 | 75.0 ± 32.4 | 15.0 ± 8.4 | 157.5 ± 6.6 | 120.0 ± 5.9 | 158.5 ± 7.4 | 45.1 ± 18.6 |
| 30 | 91.5 ± 26.9 | 8.3 ± 3.2 | 154.0 ± 6.6 | 117.5 ± 6.5 | 156.5 ± 5.9 | 57.6 ± 16.0 |
| 100 | 95.0 ± 23.3 | 13.7 ± 5.6 | 147.5 ± 7.6 | 113.0 ± 7.3 | 148.5 ± 6.0 | 62.5 ± 13.3 |
| 300 | 111.0 ± 10.9 | 27.4 ± 7.8 | 140.0 ± 7.4 | 107.5 ± 7.4 | 142.0 ± 6.5 | 77.8 ± 4.8 |

ICP = intracavernous pressure;
DT = duration of tumescence;
SBP, DBP = systolic and diastolic blood pressure,
$SBP_{ICP}$ = SBP measured at the time of maximal ICP value

TABLE 7

Effects on intracavernous pressure and blood pressure after intracavernous injection of Compound B in anaesthetised dogs (n = 6)

| DOSE (µg/kg) | ICP (mmHg) | DT (min) | SBP (mmHg) | DBP (mmHg) | $SBP_{ICP}$ (mmHg) | ICP/BP RATIO |
|---|---|---|---|---|---|---|
| BASAL | 190 ± 1.6 | — | 152.3 ± 7.5 | 112.0 ± 5.3 | — | 12.8 ± 1.7 |
| 3 | 36.7 ± 2.2 | 2.5 ± 0.9 | 151.7 ± 7.3 | 110.7 ± 5.5 | 153.3 ± 7.0 | 24.2 ± 2.0 |
| 30 | 49.3 ± 14.2 | 4.3 ± 2.0 | 150.0 ± 5.9 | 107.3 ± 4.2 | 151.0 ± 5.7 | 32.3 ± 8.6 |
| 100 | 52.7 ± 13.0 | 4.4 ± 1.6 | 146.0 ± 4.8 | 104.3 ± 4.2 | 147.3 ± 5.0 | 36.0 ± 8.5 |
| 300 | 57.3 ± 11.4 | 3.5 ± 1.1 | 139.0 ± 6.6 | 98.0 ± 6.9 | 147.3 ± 5.7 | 39.4 ± 8.0 |
| 1000 | 93.3 ± 6.2 | 41.7 ± 11.6 | 121.7 ± 4.9 | 81.0 ± 4.3 | 135.7 ± 6.8 | 69.0 ± 4.3 |

ICP = intracavernous pressure;
DT = duration of tumescence;
SBP, DBP = systolic and diastolic blood pressure,
$SBP_{ICP}$ = SBP measured at the time of maximal ICP value

TABLE 8

Effects on intracavernous pressure and blood pressure after intracavernous injection of prazosin in anaesthetised dogs (n = 4)

| DOSE (µg/kg) | ICP (mmHg) | DT (min) | SBP (mmHg) | DBP (mmHg) | $SBP_{ICP}$ (mmHg) | ICP/BP RATIO |
|---|---|---|---|---|---|---|
| BASAL | 16.0 ± 1.6 | — | 159.5 ± 3.7 | 130.5 ± 3.3 | — | 10.0 ± 0.8 |
| 30 | 25.5 ± 6.3 | 1.1 ± 1.1 | 140.0 ± 7.0 | 116.0 ± 2.9 | 142.5 ± 5.9 | 18.5 ± 5.5 |
| 100 | 27.0 ± 8.7 | 1.4 ± 1.1 | 122.0 ± 1.4 | 98.5 ± 1.9 | 130.0 ± 6.1 | 21.2 ± 7.2 |
| 300 | 37.5 ± 5.0 | 3.0 ± 1.5 | 102.0 ± 1.6 | 78.5 ± 3.5 | 117.0 ± 6.6 | 32.4 ± 4.9 |
| 1000 | 52.5 ± 5.0 | 17.7 ± 14.1 | 93.5 ± 1.9 | 59.0 ± 5.1 | 107.0 ± 8.9 | 49.8 ± 5.8 |

ICP = intracavernous pressure;
DT = duration of tumescence;
SBP, DBP = systolic and diastolic blood pressure,
$SBP_{ICP}$ = SBP measured at the time of maximal ICP value

TABLE 9

Effects on intracavernous pressure and blood pressure after intracavernous injection of phentolamine in anaesthetised dogs (n = 3)

| DOSE (μg/kg) | ICP (mmHg) | DT (min) | SBP (mmHg) | DBP (mmHg) | $SBP_{ICP}$ (mmHg) | ICP/BP RATIO |
|---|---|---|---|---|---|---|
| BASAL | 20.0 ± 2.3 | — | 166.7 ± 10.9 | 128.0 ± 8.0 | — | 11.9 ± 0.7 |
| 10 | 24.0 ± 0.0 | — | 166.7 ± 10.7 | 125.3 ± 9.4 | 166.7 ± 10.7 | 14.5 ± 0.9 |
| 30 | 20.0 ± 2.3 | — | 165.3 ± 7.3 | 125.3 ± 7.3 | 166.7 ± 9.7 | 11.9 ± 0.8 |
| 100 | 17.3 ± 1.3 | — | 159.3 ± 12.5 | 118.7 ± 11.2 | 165.3 ± 9.3 | 10.5 ± 0.2 |
| 300 | 16.0 ± 2.3 | — | 138.0 ± 16.3 | 108.7 ± 11.1 | 149.3 ± 9.3 | 10.6 ± 0.9 |
| 1000 | 62.7 ± 24.3 | 4.2 ± 2.1 | 126.0 ± 13.0 | 91.3 ± 14.7 | 141.3 ± 17.3 | 41.3 ± 12.5 |

ICP = intracavernous pressure;
DT = duration of tumescence;
SBP, DBP = systolic and diastolic blood pressure,
$SBP_{ICP}$ = SBP measured at the time of maximal ICP value The results from Examples 10 and 11 show the usefulness of selective $\alpha_{1b}$-antagonists for the treatment of erectile dysfunction.

Compound A, both in dogs and rats, and Compound B, in dogs, induced a dose-dependent increase in ICP with very low hypotensive effects. The proerectile activity of such compounds was obtained at doses lower than those of phentolamine and prazosin and the decrease in diastolic blood pressure was lower than that induced by the reference drugs.

Phentolamine increased ICP in dogs and rats at very high doses, and its proerectile activity was accompanied by sustained hypotension.

In a similar way, prazosin in dogs induced an increase in ICP accompanied by strong hypotension. In rats, prazosin did not increase intracavernous pressure when delivered intracavernously and, therefore, has no proerectile properties in this animal species.

Furthermore, the duration of action observed after injection of Compound A (and Compound B at the highest dose tested) in dogs was higher than that of the reference compounds tested.

EXAMPLE 12
Evaluation of Effect on Vaginal and Clitoral Pressure in Female Rabbits The method to evaluate the effects of the products of the invention on vaginal and clitoral pressure in females is that described by Park K et al., Int. J. Impot. Res. 9, 27–37 (1997), modified as appropriate.

Female rabbits of the New Zealand strain were anaesthetised with phenobarbital and catheterised in the carotid artery to record blood pressure. The abdominal aortas and iliac arteries, on which electromagnetic flow sensors were placed to measure peripheral flow, and the branch of pelvic nerve which innervates the vagina and clitoris were exposed and isolated by median laparotomy. The pressure in the vaginal wall and clitoris was measured by inserting needles (gauge 21G), connected to a pressure transducer, in the vaginal corpus spongiusum and clitoral corpora cavernosa respectively. The test compounds were administered locally into the subepithelial layer of the vaginal spongy tissue or administered intravenously.

The effect on vaginal and clitoral pressure after local administration and the effect on pressure induced by electrical stimulation of the pelvic nerve (stimulation parameters: 10 V, 16 Hz, 8 msec) were measured.

In the above experimental models, the results obtained with the compounds of the invention indicate effective use in the treatment of sexual dysfunction in the presence of very few side effects of a hypotensive origin.

What is claimed is:

1. A method for the treatment of female sexual dysfunction in a patient suffering from this disorder comprising the step of administering to said patient an effective amount of the compound 4-amino-6,7-dimethoxy-2-[4-[(2-isopropyl-6-methoxyphenoxy)acetyl]-1-piperazinyl]quinazoline, or a pharmaceutically acceptable salt thereof.

2. The method of claim 1 further comprising administering to said patient a prostaglandin, a direct vasodilator or a 5 cGMP phosphodiesterase inhibitor.

3. The method of claim 1 further comprising administering sildenafil to said patient.

4. The method of claim 1 wherein the compound is administered transdermally.

5. The method of claim 1 wherein the compound is administered transmucosally.

6. The method of claim 1 wherein the compound is administered orally.

7. The method of claim 1 wherein the compound is administered intravenously.

* * * * *

UNITED STATES PATENT AND TRADEMARK OFFICE
CERTIFICATE OF CORRECTION

PATENT NO. : 6,953,800 B2 Page 1 of 1
APPLICATION NO. : 09/935288
DATED : October 11, 2005
INVENTOR(S) : Leonardi et al.

It is certified that error appears in the above-identified patent and that said Letters Patent is hereby corrected as shown below:

On the title page: Item [75] should read -- Amedeo Leonardi , Milan (IT)
Rodolfo Testa, Vignate (IT)
Giorgio Sironi, Pieve Emanuele (IT)

Signed and Sealed this

Twenty-fourth Day of October, 2006

JON W. DUDAS
*Director of the United States Patent and Trademark Office*